United States Patent
Hingwe et al.

(10) Patent No.: US 9,295,525 B2
(45) Date of Patent: Mar. 29, 2016

(54) PHANTOM DEGREES OF FREEDOM FOR MANIPULATING THE MOVEMENT OF SURGICAL SYSTEMS

(71) Applicant: Intuitive Surgical Operations, Inc., Sunnyvale, CA (US)

(72) Inventors: Pushkar Hingwe, Los Altos, CA (US); Samuel Kwok Wai Au, Mountain View, CA (US); Raymond A. Bonneau, San Francisco, CA (US); Nicola Diolaiti, Menlo Park, CA (US); Arjang M. Hourtash, Santa Clara, CA (US); Amy E. Kerdok, San Jose, CA (US); Michael Turner, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 34 days.

(21) Appl. No.: 13/966,437

(22) Filed: Aug. 14, 2013

(65) Prior Publication Data
US 2014/0052151 A1    Feb. 20, 2014

Related U.S. Application Data

(60) Provisional application No. 61/683,576, filed on Aug. 15, 2012.

(51) Int. Cl.
*A61B 19/00* (2006.01)

(52) U.S. Cl.
CPC ......... *A61B 19/2203* (2013.01); *A61B 19/5212* (2013.01); *A61B 2019/2223* (2013.01)

(58) Field of Classification Search
CPC ........... A61B 19/2203; A61B 19/5212; A61B 2019/2223
See application file for complete search history.

(56) References Cited

U.S. PATENT DOCUMENTS

| 5,550,953 A | 8/1996 | Seraji |
| 6,317,651 B1 | 11/2001 | Gerstenberger et al. |

(Continued)

FOREIGN PATENT DOCUMENTS

| WO | WO-2012049623 A1 | 4/2012 |
| WO | WO-2014028557 A1 | 2/2014 |

OTHER PUBLICATIONS

Albu-Schaffer, Alin and Gerd Hirzinger, "Cartesian Impedance Control Techniques for Torque Controlled Light-Weight Robots," IEEE International Conference on Robotics and Automation, IEEE, 2002, vol. 1, pp. 657-663.

(Continued)

*Primary Examiner* — Khoi Tran
*Assistant Examiner* — Ryan Rink

(57) ABSTRACT

Methods, apparatus, and systems for performing minimally invasive surgery through an aperture of a patient. In accordance with a method, parameters are received from an input device associated with a surgeon, the parameters indicating a desired state of an end effector of a surgical instrument oriented through the aperture. The surgical instrument is included in a mechanical assembly having a first set of joints. Instructions are then computed for controlling the mechanical assembly using the received parameters by computing instructions for controlling a second set joints, the second set of joints including the first set of joints and an additional joint, the additional joint being absent from the mechanical assembly. The mechanical assembly is then driven so as to move the end effector toward the desired state based on the computed instructions.

12 Claims, 17 Drawing Sheets

(56) References Cited

U.S. PATENT DOCUMENTS

| | | | |
|---|---|---|---|
| 6,424,885 B1* | 7/2002 | Niemeyer et al. | 700/245 |
| 6,493,608 B1 | 12/2002 | Niemeyer | |
| 6,668,466 B1* | 12/2003 | Bieg et al. | 33/503 |
| 6,699,177 B1 | 3/2004 | Wang et al. | |
| 7,155,316 B2 | 12/2006 | Sutherland et al. | |
| 7,688,016 B2 | 3/2010 | Aghili | |
| 8,004,229 B2 | 8/2011 | Nowlin et al. | |
| 9,052,710 B1* | 6/2015 | Farwell | |
| 2006/0293790 A1 | 12/2006 | Gienger | |
| 2007/0013336 A1 | 1/2007 | Nowlin et al. | |
| 2007/0173977 A1 | 7/2007 | Schena | |
| 2011/0190937 A1 | 8/2011 | Ortmaier | |
| 2011/0276059 A1 | 11/2011 | Nowlin et al. | |
| 2012/0041263 A1 | 2/2012 | Sholev | |
| 2012/0078053 A1 | 3/2012 | Phee et al. | |
| 2012/0191247 A1 | 7/2012 | Kishi | |
| 2014/0052152 A1 | 2/2014 | Au et al. | |
| 2014/0052298 A1 | 2/2014 | Hourtash et al. | |

OTHER PUBLICATIONS

International Search Report and Written Opinion for Application No. PCT/US13/54834, mailed on Nov. 6, 2013, 10 pages.

International Search Report and Written Opinion for Application No. PCT/US13/54845, mailed on Nov. 25, 2013, 11 pages.

Khatib O., "A Unified Approach for Motion and Force Control of Robot Manipulators: The Operational Space Formulation," IEEE Journal of Robotics and Automation, 1987, vol. Ra-3 (1), pp. 43-53.

Michelin M., et al., "Dynamic Task/Posture Decoupling for Minimally Invasive Surgery Motions," Intelligent Robots and Systems, 2004, vol. 4, pp. 3625-3630.

Non-Final Office Action mailed Jan. 8, 2015 for U.S. Appl. No. 13/966,406, filed Aug. 14, 2013, 12 pages.

Non-Final Office Action mailed Jan. 13, 2015 for U.S. Appl. No. 13/966,494, filed Aug. 14, 2013, 12 pages.

International Search Report and Written Opinion for Application No. PCT/US13/54838, mailed on Nov. 25, 2013, 15 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

"U.S. Appl. No. 13/966,406, Response filed Apr. 7, 2015 to Non Final Office Action mailed Jan. 8, 2015", 10 pgs.

"International Application Serial No. PCT/US2013/54838, International Search Report mailed Nov. 25, 2013", 4 pgs.

"International Application Serial No. PCT/US2013/54838, Written Opinion mailed Nov. 25, 2013", 9 pgs.

Final Office Action mailed Jun. 19, 2015 for U.S. Appl. No. 13/966,494, filed Aug. 14, 2013, 6 pages.

Final Office Action mailed May 27, 2015 for U.S. Appl. No. 13/966,406, filed Aug. 14, 2013, 9 pages.

International Preliminary Report on Patentability for Application No. PCT/US2013/054834, mailed on Feb. 2, 2015, 6 pages.

Office Action mailed Apr. 30, 2015 for European Application No. 13829252.9 filed on Aug. 14, 2013, 3 pages.

Response filed Apr. 7, 2015 to Non Final Office Action mailed Jan. 18, 2015 for U.S. Appl. No. 13/966,406, filed Aug. 14, 2013, 10 pages.

Advisory Action mailed Sep. 3, 2015 for U.S. Appl. No. 13/966,406, filed Aug. 14, 2013, 3 pages.

Advisory Action mailed Sep. 10, 2015 for U.S. Appl. No. 13/966,494, filed Aug. 14, 2013, 6 pages.

Notice of Allowance mailed Oct. 8, 2015 for U.S. Appl. No. 13/966,494, filed Aug. 14, 2013, 5 pages.

Notice of Allowance mailed Oct. 19, 2015 for U.S. Appl. No. 13/966,406, filed Aug. 14, 2013, 5 pages.

Response filed Apr. 13, 2015 to Non-final office action mailed Jan. 13, 2015 for U.S. Appl. No. 13/966,494, filed Aug. 14, 2013, 15 pages.

Response filed Aug. 19, 2015 to Final office action mailed Jun. 19, 2015 for U.S. Appl. No. 13/966,494, filed Aug. 14, 2013, 9 pages.

Response filed Aug. 19, 2015 to Final Office Action mailed May 27, 2015 for U.S. Appl. No. 13/966,406, filed Aug. 14, 2013, 8 pages.

Response filed Sep. 21, 2015 to Advisory Action mailed Sep. 10, 2015 for U.S. Appl. No. 13/966,494, filed Aug. 14, 2013, 3 pages.

* cited by examiner

PHANTOM DEGREES OF FREEDOM FOR MANIPULATING THE MOVEMENT OF SURGICAL SYSTEMS

CROSS-REFERENCES TO RELATED APPLICATIONS

This application claims the benefit of U.S. Provisional Application No. 61/683,576, filed Aug. 15, 2012, which is incorporated by reference herein in its entirety for all purposes.

The present application is generally related to the following commonly-owned applications: U.S. Provisional Application No. 61/654,764 filed Jun. 1, 2012, entitled "Commanded Reconfiguration of a Surgical Manipulator Using the Null Space", U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" and U.S. application Ser. No. 09/398,507 filed Sep. 17, 1999 (U.S. Pat. No. 6,714,839), entitled "Master Having Redundant Degrees of Freedom," the disclosures of which are incorporated herein by reference in their entireties.

BACKGROUND

Embodiments of the present invention generally provide improved surgical and/or robotic devices, systems, and methods.

Minimally invasive medical techniques are aimed at reducing the amount of extraneous tissue which is damaged during diagnostic or surgical procedures, thereby reducing patient recovery time, discomfort, and deleterious side effects. Millions of surgeries are performed each year in the United States. Many of these surgeries can potentially be performed in a minimally invasive manner. However, only a relatively small number of surgeries currently use these techniques due to limitations in minimally invasive surgical instruments and techniques and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, such apertures resulting in the trauma typically associated with open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Provisional Application No. 61/654,764 filed Jun. 1, 2012, entitled "Commanded Reconfiguration of a Surgical Manipulator Using the Null Space", and U.S. Pat. Nos. 6,758,843; 6,246,200; and 5,800,423, the full disclosures of which are incorporated herein by reference in their entirety. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing dangerous forces against the abdominal wall. Alternative manipulator structures are described, for example, in U.S. Pat. Nos. 7,594,912; 6,702,805; 6,676,669; 5,855,583; 5,808,665; 5,445,166; and 5,184,601, the full disclosures of which are incorporated herein by reference in their entirety.

While the new robotic surgical systems and devices have proven highly effective and advantageous, still further improvements would be desirable. In some cases, the master controller(s) used by the surgeon have a number of degrees of freedom more than or equal to the number of degrees of freedom which the end effectors of the remotely controlled robotic manipulator arms and/or tools have. In such cases, controllers that are used to control the robotic manipulator arms and/or tools may become overconstrained. For example, where the remote tool is a rigid endoscope extending through a minimally invasive aperture, two orientational degrees of freedom may not be available within the workspace (those associated with a tool wrist near an end effector, e.g., wrist pitch and yaw). Accordingly, the robotic manipulator with endoscope only has four degrees of freedom at its tip. In practice, these mathematical problems can become tangible, resulting in a sluggish, unresponsive feel to the surgeon which is undesirable. Further problems can arise when tools having different degrees of freedom are used with the same robotic surgical manipulator. For example, a surgeon may wish to use jaws having three degrees of freedom, and then replace the jaws with a suction device having two degree of freedom. Even further problems can arise when using estimated joint positions to control tool movements in situations where input and output degrees of freedom differ. Such situations may result in numerical errors being imposed into the joint position estimations resulting in undesired tool movements.

For these and other reasons, it would be advantageous to provide improved devices, systems, and methods for surgery, robotic surgery, and other robotic applications. It would be particularly beneficial if these improved technologies provided the ability to effectively control robotic manipulator arms and/or tools with end effectors having a number of degrees of freedom fewer than the number of degrees of freedom of a master controller manipulated by a surgeon. It would be even more beneficial if these improved technologies allowed the same computation engine to be used for all instruments of the robotic system, thereby reducing controller complexity and costs while increasing flexibility.

BRIEF SUMMARY

Embodiments of the present invention generally provide improved robotic and/or surgical devices, systems, and methods. In one embodiment, a method of operating a surgical system is disclosed. The method includes various operations, including receiving parameters from an input device associated with a surgeon, the parameters indicating a desired state of an end effector of a surgical instrument oriented through the aperture, and the surgical instrument being included in a mechanical assembly having a first set of joints. The method also includes computing instructions for controlling the mechanical assembly using the received parameters by computing instructions for controlling a second set joints, the second set of joints including the first set of joints and an additional joint, the additional joint being absent from the mechanical assembly. The method further includes driving the mechanical assembly so as to move the end effector toward the desired state based on the computed instructions.

In accordance with another embodiment, a surgical system for performing minimally invasive surgery through an aperture of a patient is disclosed. The system includes a surgeon's console including an input device for receiving an input from the surgeon. The system also includes at least one manipulator structure operable to receive a first surgical instrument and a second surgical instrument, the first surgical instrument having a number of degrees of freedom different than a number of degrees of freedom of the second surgical instrument. The system further includes a controller for controlling an instrument coupled to the at least one manipulator structure. In some embodiments, the controller may be operable to control the first surgical instrument and the second surgical instrument using a first kinematic model of the first instrument and a second kinematic model of the second instrument.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

Figure 1A:
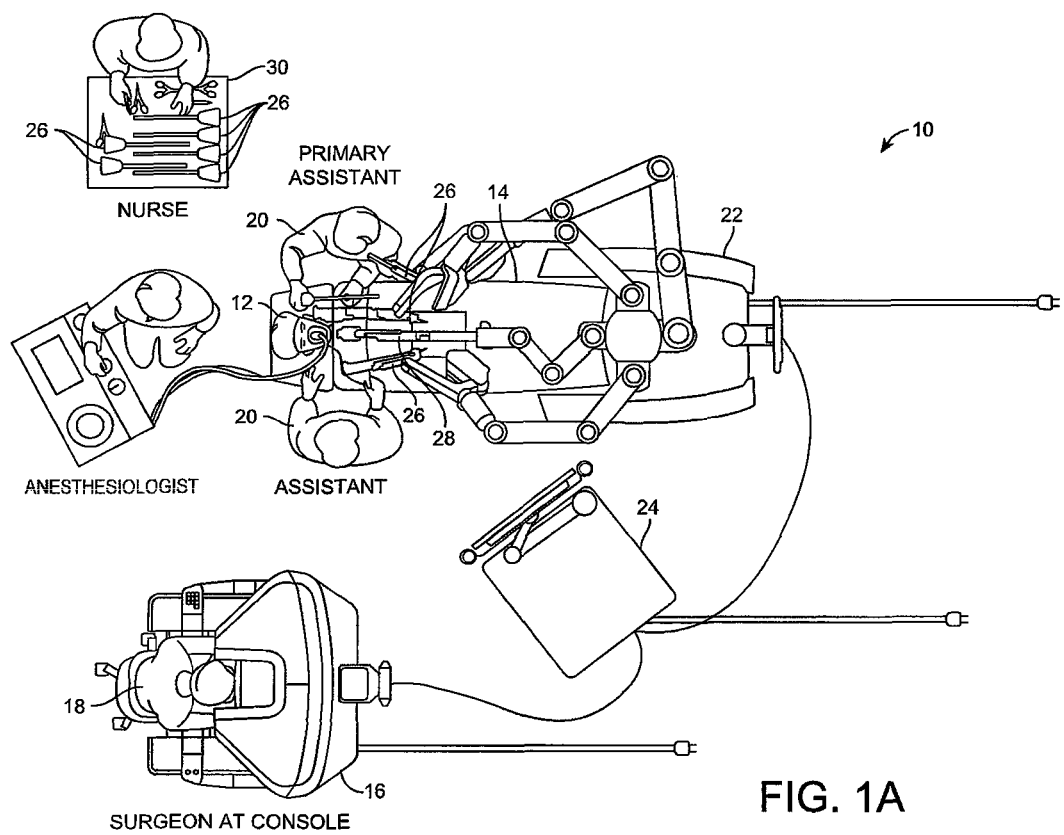
FIG. 1A is an overhead view of a robotic surgical system in accordance with embodiments of the present invention.

Embodiments of the present invention generally provide improved techniques for controlling the movement of mechanical bodies. Some embodiments are particularly advantageous for use with surgical robotic systems in which a plurality of surgical tools or instruments are mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector which is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. For example, the manipulator assembly may include kinematic degrees of freedom of a manipulator as well as kinematic degrees of freedom of a tool connected to the manipulator. The combination of these may be referred to herein as "manipulator degrees of freedom", and are typically defined in joint space (described below). Actuation of the end effector (such as opening or closing of the jaws of a gripping device, energizing an electrosurgical paddle, activating air pressure for a vacuum, or the like) will often be separate from, and in addition to, these manipulator assembly degrees of freedom. These may be referred to herein as "actuation degrees of freedom".

The end effector (or, more generally, the control frame, as described below) will typically move in the workspace with between two and six degrees of freedom. The degrees of freedom of the end effector (or, more generally, the degrees of freedom of the control frame) may be referred to herein as "end effector degrees of freedom", and are typically defined in Cartesian space (described below). As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point at the aperture site.

Many of the manipulator assemblies described herein have fewer degrees of freedom available for use than those that are typically associated with full control over the positioning of an end effector in a workspace (where full control of the end effector requires end effector degrees of freedom including three independent translations and three independent orientations). That is, the manipulator assemblies may have an insufficient number or type of degrees of freedom for independently controlling the six end effector degrees of freedom. For example, a rigid endoscope tip without an articulating wrist may be missing one or two degrees of freedom at the wrist, such as wrist pitch and/or yaw. Accordingly, the endoscope may have only four or five degrees of freedom for positioning the end effector, rather than six, thus potentially constraining the motion of the endoscope.

However, some of the manipulator assemblies described herein have a greater number of degrees of freedom than that required to fully control the positioning of the end effector (where full control of the end effector requires end effector degrees of freedom including three independent translations and three independent orientations), but due to the type or arrangement of the joints of the manipulator assemblies, the manipulator assemblies still cannot fully control the positioning of the end effector. For example, a manipulator assembly may have seven manipulator degrees of freedom, but three of those are redundant. As a result, the end effector effectively has five degrees of freedom.

Regardless of the number of degrees of freedom available for controlling the position of the end effector, the manipulator assemblies described herein may also facilitate additional degrees of freedom for actuating a tool (i.e., actuation degrees of freedom). For example, the manipulator assemblies may be configured to mount a tool having an electrocautery probe operable to, e.g., heat select tissue upon activation. For another example, the manipulator assemblies may be configured to mount a tool having a vacuum operable to, e.g., apply suction forces around select tissue upon activation. In such cases, these additional degrees of freedom are not kinematic, and therefore do not affect the position (i.e., location and orientation) of the end effector.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control systems that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In many embodiments, the tool of an exemplary manipulator arm pivots about a pivot point adjacent a minimally invasive aperture. In some embodiments, the system may utilize a hardware remote center, such as the remote center kinematics described in U.S. Pat. No. 6,786,896, the entire contents of which are incorporated herein in its entirety. Such systems may utilize a double parallelogram linkage which constrains the movement of the linkages such that the shaft of the instrument supported by the manipulator pivots about a remote center point. Alternative mechanically constrained remote center linkage systems are known and/or may be developed in the future. In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a desired pivot point, as opposed to a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired.

In many configurations, robotic surgical systems may include master controller(s) having a number of degrees of freedom fewer than, more than, or equal to the number of degrees of freedom which the remotely controlled robotic manipulator arms and/or tools have. In such cases, Jacobian based or other controllers used to control the robotic manipulator arms and/or tools typically provide complete mathematical solutions and satisfactory control. For example, fully controlling the position (i.e., location and orientation) of a rigid body can employ six independently controllable degrees of freedom of the rigid body, which includes three degrees of freedom for translations and three degrees of freedom for orientations. This lends itself nicely to a Jacobian based control algorithm in which a 6×N Jacobian matrix is used.

However, when a 6×N Jacobian controller is used to control robotic manipulator arms and/or tools having fewer than 6 degrees of freedom, problems can be introduced since the mathematical problem is overconstrained. For example, where the remote tool is a rigid endoscope extending through a minimally invasive aperture (so that the endoscope pivots at the aperture), two manipulator degrees of freedom may not be available (those often associated with a tool wrist adjacent the end effector, e.g., wrist pitch and yaw. Each of these two missing manipulator degrees of freedom affects both translations and orientations of the end effector. Accordingly, the endoscope only has four independently controllable degrees of freedom at its tip (i.e., end effector degrees of freedom), which can result in the aforementioned mathematical problems for a 6×N Jacobian approach. In practice, these mathematical problems often become tangible. When, for example, the endoscope tip is commanded to either pan or tilt, since it has a non-wristed tip, it can only do one thing, and that is to do a combination of both. In other words, the endoscope tip may not be independently controlled to pan or tilt; rather, it can only perform a fixed combination of these. This can potentially result in a sluggish, unresponsive feel to the surgeon which is undesirable.

Further problems often arise when tools having different degrees of freedom are used with the same robotic surgical manipulator. For example, a surgeon may wish to use jaws having three kinematic degrees of freedom, and then replace the jaws with a suction device having two kinematic degrees of freedom. Since the mathematical model for controlling the motion of the jaws is different than that for controlling the motion of the suction device, the robotic system applies two different models to avoid the aforementioned problems resulting from the same mathematical model being used. For example, where the manipulator provides three degrees of freedom in addition to the degrees of freedom of the tool, controllers for controlling the motion of the jaws and the suction device may include a 6×N Jacobian based controller and a 5×(N−1) Jacobian based controller, respectively. The use of multiple controllers results in an added layer of complexity that may increase cost and/or limit scalability for a large set of different tools, and a 5×(N−1) Jacobian is more complicated to use due to its reduced number of rows.

Yet further problems often arise when using estimates of the current joint positions of the manipulator assembly to control subsequent movements of the joints. Joint controllers may use the combination of desired joint positions and estimates of the current joint positions to determine the appropriate torque to apply to the joints so as to move the joints closer to the desired joint positions. In situations where the number of degrees of freedom of the kinematic model of a manipulator assembly are equal to the number of degrees of freedom of the manipulator assembly, but the position of a tool tip is measured in a greater number of degrees of freedom, using those measurements as inputs to the kinematic model to determine joint angles results in errors being imposed in the resulting joint angle calculations. These errors result in undesirable control of the manipulator assembly when those joint angle calculations are used to control motion of the manipulator assembly.

Although manipulator assemblies having a variety of degrees of freedom are disclosed herein, including assemblies having fewer than, the same number as, or more than the six degrees of freedom for fully controlling the position of an end effector, many embodiments of these assemblies lack at least one degree of freedom for fully controlling the position of the end effector. While the manipulator assemblies may lack one of these degrees of freedom, the input device controlling the manipulator assembly (e.g., a master control input device) may include the lacking degree of freedom. In accordance with embodiments of the present invention, in response to an input controlling the degree(s) of freedom missing at the manipulator assembly, the other degrees of freedom available at the manipulator assembly may provide motions so as to simulate control of the missing degree(s) of freedom. This may be done by using a kinematic model of the manipulator assembly that includes and performs calculations for the missing manipulator degree(s) of freedom. By performing such calculations, the remaining degrees of freedom of the manipulator assembly may be more effectively controlled to cause an end effector to appear to move along the requested degree(s) of freedom. Further, the use of such a kinematic model may advantageously reduce the complexity of facilitating the positioning and/or actuation of tools having different numbers of degrees of freedom.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a patient 12 who is lying down on an operating table 14. The system can include a surgeon's console 16 for use by a surgeon 18 during the procedure. One or more assistants 20 may also participate in the procedure. The MIRS system 10 can further include a patient side cart 22 (surgical robot) and an electronics cart 24. The patient side cart 22 can manipulate at least one removably coupled tool assembly 26 (hereinafter simply referred to as a "tool") through a minimally invasive incision in the body of the patient 12 while the surgeon 18 views the surgical site through the console 16. An image of the surgical site can be obtained by an imaging device 28, such as a stereoscopic endoscope, which can be manipulated by the patient side cart 22 so as to orient the imaging device 28. The electronics cart 24 can be used to process the images of the surgical site for subsequent display to the surgeon 18 through the surgeon's console 16. The number of surgical tools 26 used at one time will generally depend on the diagnostic or surgical procedure and the space constraints within the operating room among other factors. If it is necessary to change one or more of the tools 26 being used during a procedure, an assistant 20 may remove the tool 26 from the patient side cart 22, and replace it with another tool 26 from a tray 30 in the operating room.

MIRS system 10 in certain embodiments is a system for performing a minimally invasive diagnostic or surgical procedure on a patient including various components such as a surgeon's console 16, an electronics cart 24, and a patient side cart 22. However, it will be appreciated by those of ordinary skill in the art that the system could operate equally well by having fewer or a greater number of components than are illustrated in FIG. 1A. Thus, the depiction of the system 10 in FIG. 1A should be taken as being illustrative in nature, and not limiting to the scope of the disclosure.

Figure 1B:
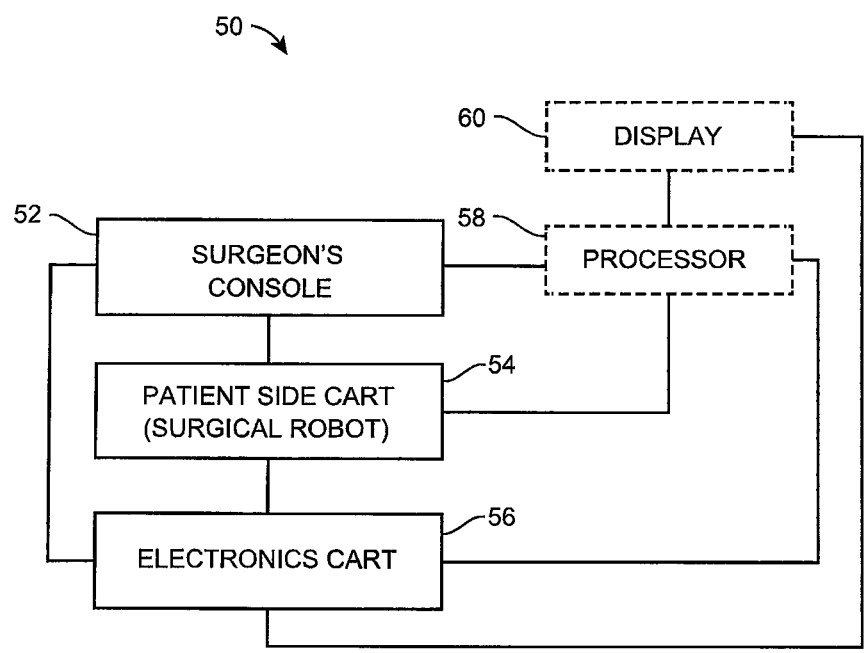
FIG. 1B diagrammatically illustrates the robotic surgical system of FIG. 1A.

FIG. 1B diagrammatically illustrates a robotic surgery system 50 (such as MIRS system 10 of FIG. 1A). As discussed above, a surgeon's console 52 (such as surgeon's console 16 in FIG. 1A) can be used by a surgeon to control a patient side cart (surgical robot) 54 (such as patient side cart 22 in FIG. 1A) during a minimally invasive procedure. The patient side cart 54 can use an imaging device, such as a stereoscopic endoscope, to capture images of the procedure site and output the captured images to an electronics cart 56 (such as the electronics cart 24 in FIG. 1A). As discussed above, the electronics cart 56 can process the captured images in a variety of ways prior to any subsequent display. For example, the electronics cart 56 can overlay the captured images with a virtual control interface prior to displaying the combined images to the surgeon via the surgeon's console 52. The patient side cart 54 can output the captured images for processing outside the electronics cart 56. For example, the patient side cart 54 can output the captured images to a processor 58, which can be used to process the captured images. The images can also be processed by a combination of the electronics cart 56 and the processor 58, which can be coupled together so as to process the captured images jointly, sequentially, and/or combinations thereof. One or more separate displays 60 can also be coupled with the processor 58 and/or the electronics cart 56 for local and/or remote display of images, such as images of the procedure site, or other related images.

MIRS system 50 in certain embodiments is a system for performing a minimally invasive diagnostic or surgical procedure on a patient including various components such as a surgeon's console 52, an electronics cart 56, and a patient side cart 54. However, it will be appreciated by those of ordinary skill in the art that the system could operate equally well by having fewer or a greater number of components than are illustrated in FIG. 1B. Thus, the depiction of the system 50 in FIG. 1B should be taken as being illustrative in nature, and not limiting to the scope of the disclosure.

Figure 2:
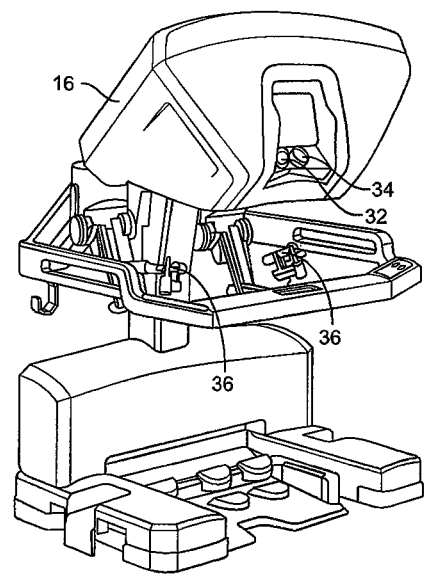
FIG. 2 is a perspective view of the surgeon console of FIG. 1A.

FIG. 2 is a perspective view of the surgeon's console 16. The surgeon's console 16 includes a left eye display 32 and a right eye display 34 for presenting the surgeon 18 with a coordinated stereo view of the surgical site that enables depth perception. The console 16 further includes one or more input control devices 36, which in turn cause the patient side cart 22 (shown in FIG. 1A) to manipulate one or more tools. The input control devices 36 can provide the same degrees of freedom, or more degrees of freedom, as their associated tools 26 (shown in FIG. 1A) so as to provide the surgeon with telepresence, or the perception that the input control devices 36 are integral with the tools 26 so that the surgeon has a strong sense of directly controlling the tools 26. To this end, position, force, and tactile feedback sensors (not shown) may be employed to transmit position, force, and tactile sensations from the tools 26 back to the surgeon's hands through the input control devices 36.

The surgeon's console 16 is usually located in the same room as the patient so that the surgeon may directly monitor the procedure, be physically present if necessary, and speak to an assistant directly rather than over the telephone or other communication medium. However, the surgeon can be located in a different room, a completely different building, or other remote location from the Patient allowing for remote surgical procedures.

Surgeon's console 16 in certain embodiments is a device for presenting the surgeon with information concerning the surgical site and receiving input information from the surgeon, and includes various components such as eyes displays and input control devices. However, it will be appreciated by those of ordinary skill in the art that the surgeon's console could operate equally well by having fewer or a greater number of components than are illustrated in FIG. 2. Thus, the depiction of the surgeon's console 16 in FIG. 2 should be taken as being illustrative in nature, and not limiting to the scope of the disclosure.

Figure 3:
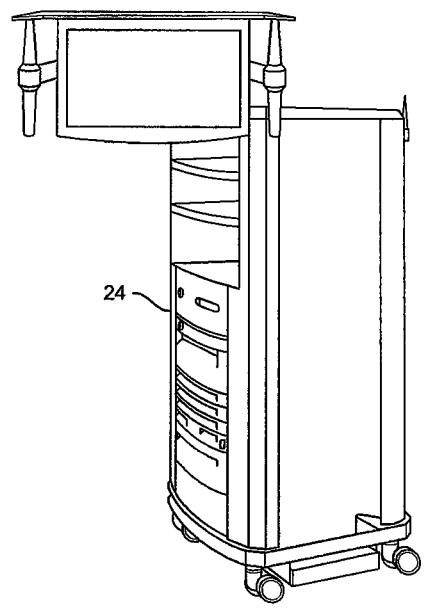
FIG. 3 is a perspective view of the electronics cart of FIG. 1A.

FIG. 3 is a perspective view of the electronics cart 24. The electronics cart 24 can be coupled with the imaging device 28 and can include a processor to process captured images for subsequent display, such as to a surgeon on the surgeon's console, or on another suitable display located locally and/or remotely. For example, where a stereoscopic endoscope is used, the electronics cart 24 can process the captured images so as to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

The electronics cart 24 in certain embodiments is a device for presenting information concerning a surgery to a surgical team and includes various components displays, processors, storage elements, etc. However, it will be appreciated by those of ordinary skill in the art that the electronics cart could operate equally well by having fewer or a greater number of components than are illustrated in FIG. 3. Thus, the depiction of the electronics cart 24 in FIG. 3 should be taken as being illustrative in nature, and not limiting to the scope of the disclosure.

Figure 4:
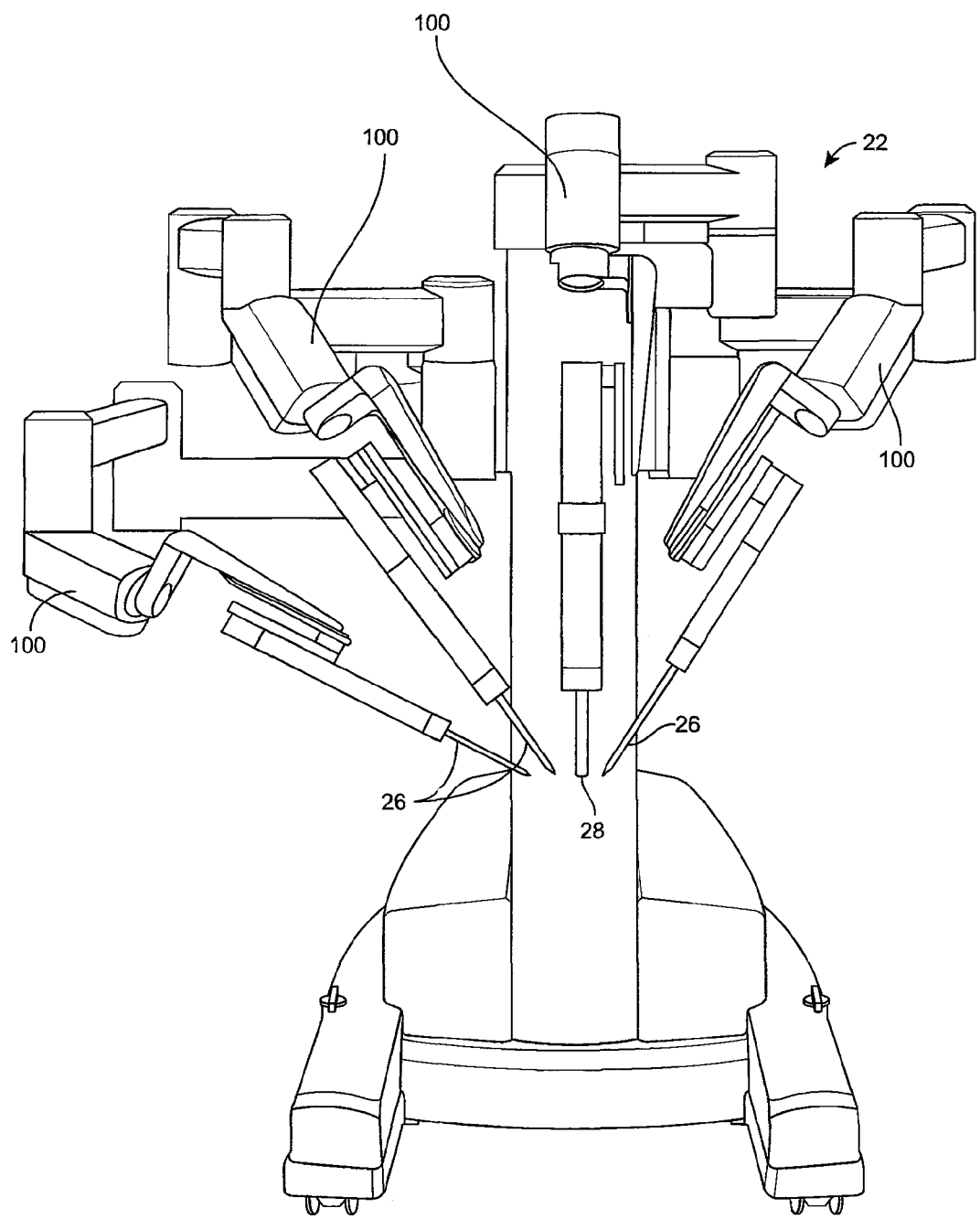
FIG. 4 is a perspective view of a patient side cart having a plurality of manipulator arms each supporting a surgical instrument.

FIG. 4 shows a patient side cart 22 having a plurality of manipulator arms, each supporting a surgical instrument or tool 26 at a distal end of the manipulator arm. The patient side cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints, where each joint provides a manipulator degree of freedom. The angle of each joint may be controlled by an actuator such as a motor or motor assembly, and in some embodiments the angle of each joint may be measured using one or more sensors (e.g., encoders, or potentiometers, or the like) disposed on or proximate to each joint. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip applier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allows the end effectors and the distal end of the shaft to be inserted distally into a surgical worksite through a minimally invasive aperture, often through an abdominal wall or the like. The surgical worksite may be insufflated, and movement of the end effectors within the patient will often be affected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside the patient 12 during a surgical procedure.

The patient side cart 22 in certain embodiments is a device for providing surgical tools for assisting in a surgical procedure on a patient, and may include various components such as manipulator arms 100 and tools 26. However, it will be appreciated by those of ordinary skill in the art that the patient side cart could operate equally well by having fewer or a greater number of components than are illustrated in FIG. 4. Thus, the depiction of the patient side cart 22 in FIG. 4 should be taken as being illustrative in nature, and not limiting to the scope of the disclosure.

Figure 5:
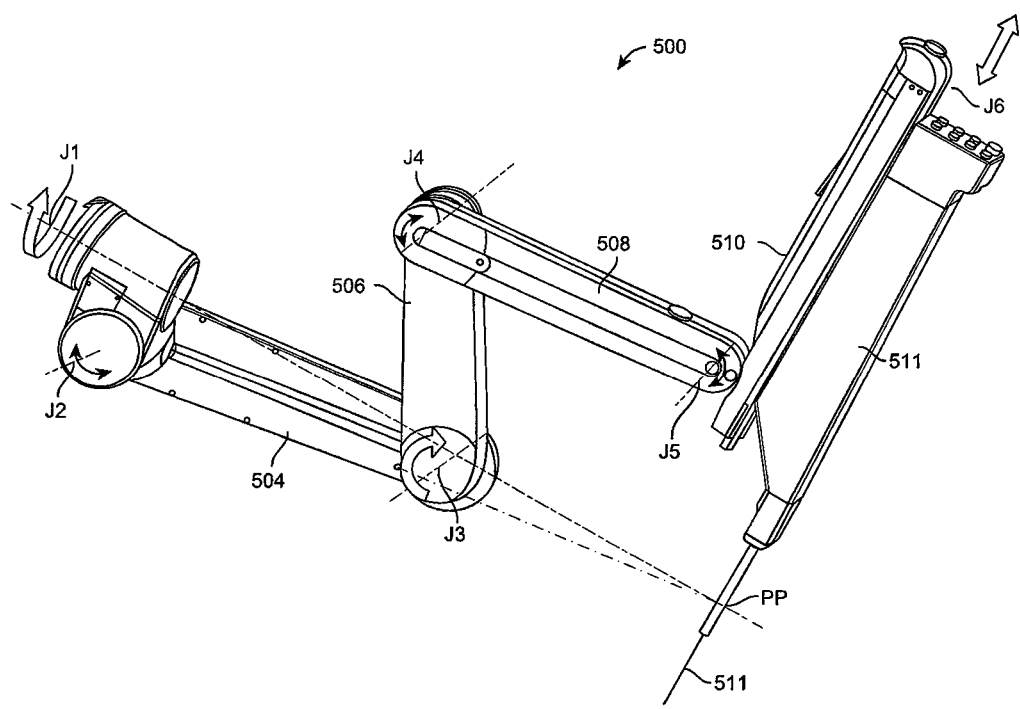
FIG. 5 is a perspective view of a manipulator arm in accordance with an embodiment.

An exemplary manipulator arm in accordance with some embodiments of the present invention can be understood with reference to FIG. 5. As described above, a manipulator arm generally supports a distal instrument or surgical tool and affects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an exemplary manipulator includes a plurality of joints having either redundant or non-redundant degrees of freedom, but is lacking at least one degree of freedom necessary to fully prescribe the position (i.e., location and orientation) of the end effector.

In many embodiments, such as that shown in FIG. 5, an exemplary manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, may have redundant degrees of freedom such that the joints of the manipulator arm can be driven into a range of differing configurations for a given end effector position. For example, the manipulator arm of FIG. 5 may be maneuvered into differing configurations while the distal instrument or tool 511 supported within the instrument holder 510 maintains a particular state, which may include a given position or velocity of the end effector. In some embodiments, the joints of the manipulator are not operable to independently control at least one of the six end effector degrees of freedom that fully define the position of the tool 511. For example, the manipulator may not be operable to cause the tool 511 to independently roll, pitch, yaw, and/or translate in one or more directions.

Describing the individual links of manipulator arm 500 of FIG. 5 along with the axes of rotation of the joints connecting the links as illustrated in FIG. 5, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. Typically, the pivotal axes of each of joints J2, J3, J4, and J5 are substantially parallel and the linkages appear "stacked" when positioned next to one another, so as to provide a reduced width of the manipulator arm and improve patient clearance during maneuvering of the manipulator assembly. In many embodiments, the instrument holder 510 also includes additional joints, such as a prismatic joint J6 that facilitates axial movement of the instrument 511 through the minimally invasive aperture and facilitates attachment of the instrument holder 510 to a cannula through which the instrument 511 is slidably inserted. In some embodiments, even when combining the degrees of freedom of the instrument holder 510 with the rest of those of manipulator arm 500, the resulting degrees of freedom are still insufficient to provide at least one of the six degrees of freedom necessary to fully define the position of the tool 511.

The instrument 511 may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, instrument 511 includes a rotational joint J7 (not shown) near or proximal of the insertion point of the tool tip or the pivot point PP, which generally is disposed at the site of a minimally invasive aperture. A distal wrist of the instrument allows pivotal motion of an end effector of surgical tool 511 about instrument joints axes of one or more joints at the instrument wrist. An angle between end effector jaw elements may be controlled independently of the end effector location and orientation. Notwithstanding these additional kinematic degrees of freedom provided by the surgical tool 511, which may be considered to be part of the manipulator degrees of freedom, in some embodiments, even when combining the kinematic degrees of freedom of the surgical tool 511 with those of manipulator arm 500 (including, e.g., those of instrument holder 510), the resulting kinematic degrees of freedom are still insufficient to fully control the position of the tip of tool 511.

The manipulator arm 500 in certain embodiments is a mechanical body for holding and controlling a tool, and may include a number of links and joints. However, it will be appreciated by those of ordinary skill in the art that the manipulator arm could operate equally well by having fewer or a greater number of components than are illustrated in FIG. 5. Thus, the depiction of the manipulator arm 500 in FIG. 5 should be taken as being illustrative in nature, and not limiting to the scope of the disclosure.

Figure 6A:
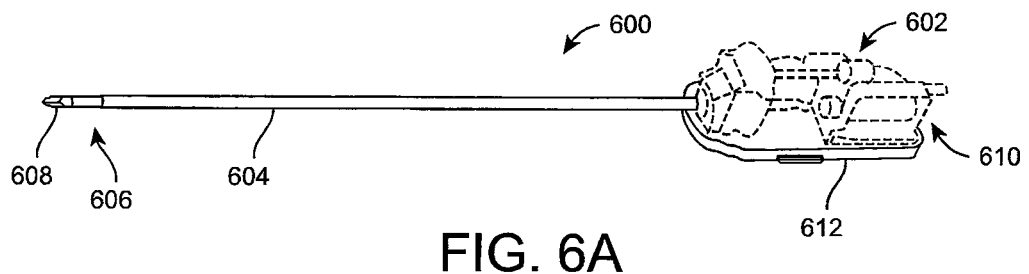
FIG. 6A is a perspective view of a robotic surgery tool that includes an end effector having opposing clamping jaws in accordance with an embodiment.

FIG. 6A shows a surgical tool 600 that includes a proximal chassis 602, an instrument shaft 604, and a distal end effector 606 having a jaw 608 that can be articulated to grip a patient tissue. The proximal chassis includes an input coupler that is configured to interface with and be driven by an output coupler of the patient side cart 22 (FIG. 1A). The input coupler is drivingly coupled with an input link of a spring assembly 610. The spring assembly 610 is mounted to a frame 612 of the proximal chassis 602 and includes an output link that is drivingly coupled with a drive shaft that is disposed within the instrument shaft 604. The drive shaft is drivingly coupled with the jaw 608.

In accordance with some embodiments and as shown in FIG. 6A, the surgical tool 600 may not include any degrees of freedom for altering a position of the end effector 606. In other embodiments, the surgical tool 600 may include one or more joints for adding degrees of freedom for altering the position of the end effector 606. For example, the instrument shaft 604 may include joints for changing a pitch and/or yaw of the end effector 606. Further, in some embodiments and as shown in FIG. 6A, the surgical tool 600 may include one or more degrees of freedom for actuating the end effector 606. For example, the spring assembly 610 may be operable to actuate the jaw 608. Additional characteristics of surgical tool 600, as well as other surgical tools, are described in commonly-owned U.S. application Ser. No. 13/297,158, filed Nov. 15, 2011, entitled "Method for Passively Decoupling Torque Applied By a Remote Actuator Into an Independently Rotating Member," the disclosure of which is incorporated herein by reference in its entirety.

Figure 6B:
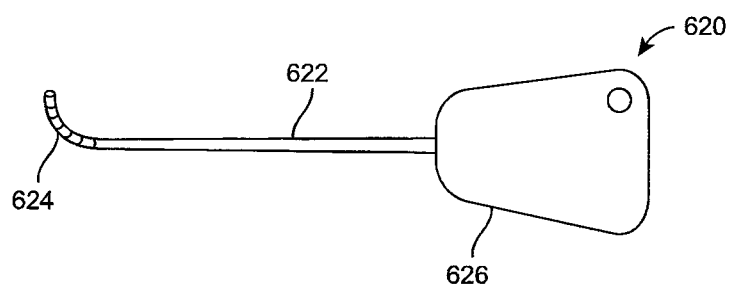
FIG. 6B illustrates a wristed endoscope in accordance with an embodiment.

FIG. 6B illustrates a wristed endoscope 620 that may, in some embodiments, be used in robotic minimally invasive surgery. The endoscope 620 includes an elongate shaft 622 and a flexible wrist 624 located at the working end of the shaft 622. A housing 626 allows the surgical instrument 620 to releasably couple to a manipulator located at the opposite end of the shaft 624. An endoscopic camera lens is implemented at the distal end of the flexible wrist 624. A lumen (not shown) runs along the length of the shaft 622 which connects the distal end of the flexible wrist 624 to the housing 626. In a "fiber scope" embodiment, imaging sensor(s) of the endoscope 620, such as charge coupled devices (CCDs), may be mounted inside the housing 626 with connected optical fibers running inside the lumen along the length of the shaft 622 and ending at substantially the distal end of the flexible wrist 624. In an alternate "chip-on-a-stick" embodiment, the imaging sensor(s) of the endoscope 620 may be mounted at the distal end of the flexible wrist 624. The imaging sensor(s) may be two-dimensional or three-dimensional.

In some embodiments, the flexible wrist 624 may have at least one degree of freedom to allow the endoscope 620 to articulate and maneuver easily around internal body tissues, organs, etc. to reach a desired destination (e.g., epicardial or myocardial tissue). The housing 626 may house a drive mechanism for articulating the distal portion of the flexible wrist 624. The drive mechanism may be cable-drive, gear-drive, belt drive, or another type of drive mechanism suitable to drive the flexible wrist 624 along its degree(s) of freedom. For example, in one embodiment, the flexible wrist 624 may have two translation degrees of freedom and the shaft 622 may be operable to rotate around an axis along the length of the shaft 622. In some medical procedures, the articulate endoscope 620 maneuvers and articulates around internal organs, tissues, etc. to acquire visual images of hard-to-see and/or hard-to-reach places. Additional characteristics of the endoscope 620, as well as other surgical tools, are described in commonly-owned U.S. application Ser. No. 11/319,011, filed Dec. 27, 2005, entitled "Articulate and Swapable Endoscope for a Surgical Robot," the disclosure of which is incorporated herein by reference in its entirety.

Figure 6C:
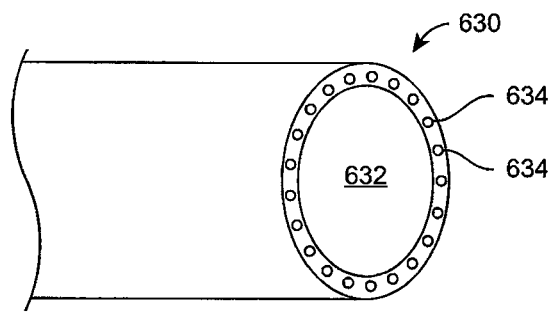
FIG. 6C is a perspective view of the distal end of an overtube with suction ports in accordance with an embodiment.

FIG. 6C is a perspective view of the distal end of an overtube with suction ports. The overtube 630 defines an instrument lumen 632 which extends through the overtube 630 to permit passage of an instrument. The overtube 630 further comprises one or more suction passages 634 which are coupled to a vacuum source. The overtube 630 may, in various embodiments, be formed out of any of a variety of materials suitable for surgical use and may be provided with any of variety of stiffnesses. For example, the overtube 630 may comprise a substantially rigid material, may comprise a flexible material, or may comprise a combination of one or more substantially rigid portions and one or more flexible portions to provide a bendable structure. The cross-sectional shape of the overtube 630 may also vary. In the illustrated embodiment, the overtube 630 has a substantially circular cross-sectional shape and is made out of polyurethane. In other embodiments, other cross-sectional shapes may be used, such as, e.g., oval, rectangular, triangular, etc., depending on the application.

In the illustrated embodiment, the suction passages 634 comprise a plurality of vacuum lumens within the wall of the overtube 630, with each vacuum lumen being coupled to the vacuum source (not shown). The vacuum source may be operated to create a vacuum pressure in each suction passage 634, thereby creating a suction force onto a tissue surface which the suction passages 634 are in contact with. As a result of this suction force, the overtube 630 will be attached to the tissue surface. If the vacuum pressure is discontinued, the tissue surface will be released and the overtube 630 will no longer be attached to the tissue. Accordingly, by controllably providing a suction force via the suction passages 634, the overtube 630 can be releasably attached to patient's tissue surface. A surgical instrument, such as an irrigation tool, cutting tool, etc., may then be inserted through the instrument lumen 200 to treat tissue disposed within the instrument lumen 632.

In accordance with some embodiments, the overtube 630 may be made of substantially rigid material and not include any degrees of freedom for altering a position of the overtube 630. In other embodiments, the overtube 630 may include one or more joints for adding degrees of freedom for altering the position of the distal end of the overtube 630. For example, the overtube 630 may include joints for changing a pitch and/or yaw of the distal end of the overtube 630. Further, in some embodiments, the overtube 630 may include one or more degrees of freedom for actuating functionality of the overtube 630. For example, a vacuum source (not shown) may be operable to create or remove a vacuum pressure in one or more suction passages 634. Additional characteristics of the overtube 630, as well as other surgical tools, are described in commonly-owned U.S. application Ser. No. 11/618,374, filed Dec. 29, 2006, entitled "Vacuum Stabilized Overtube for Endoscopic Surgery," the disclosure of which is incorporated herein by reference in its entirety.

Figure 6D:
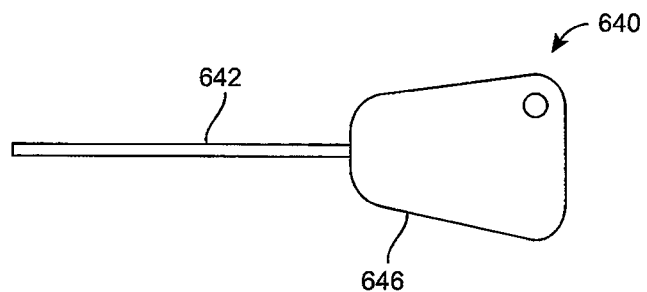
FIG. 6D illustrates a non-wristed endoscope in accordance with an embodiment.

FIG. 6D illustrates a non-wristed endoscope 640 that may, in some embodiments, be used in robotic minimally invasive surgery. The non-wristed endoscope 640 is similar to the wristed endoscope 620 depicted in and discussed with reference to FIG. 6B, and thus similarly includes a housing 646 and a shaft 622. The difference is that the non-wristed endoscope 640 does not include a flexible wrist. The non-wristed endoscope has a reduced number of degrees of freedom compared to the wristed endoscope, and in this particular example, non-wristed endoscope 640 does not have a wrist pitch or wrist yaw.

The surgical tool 600, endoscope 620, and overtube 30 are various tools that include a variety of components. However, it will be appreciated by those of ordinary skill in the art that these tools could operate equally well by having fewer or a greater number of components than are illustrated in FIGS. 6A to 6C. Further, it would will also be appreciated that other tools may also or alternatively be used, such as gripping devices, electrosurgical paddles, vacuums, irrigators, staplers, scissors, knifes, etc. Thus, the depiction of surgical tools in FIGS. 6A to 6C should be taken as being illustrative in nature, and not limiting to the scope of the disclosure.

Figure 7A:
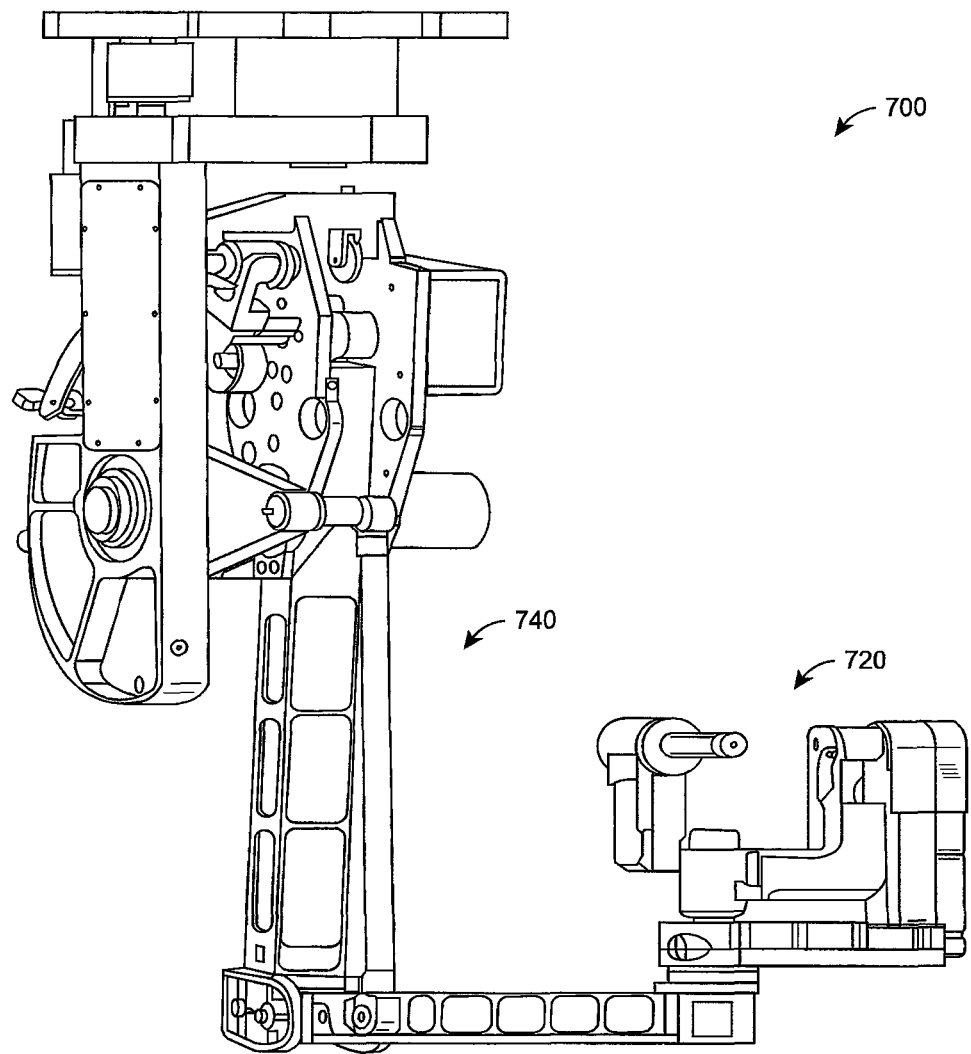
FIG. 7A is a perspective view of a master control input device in accordance with an embodiment.

FIG. 7A is a perspective view of a master control input device 700 that may be part of a surgeon's console 16 (FIG. 1A) in accordance with an embodiment. The master control 700 includes a gimbal or wrist 720 that is operatively coupled to an articulated arm 740.

Master control input device 700 has a number of degrees of freedom and is operable to control a manipulator assembly (e.g., manipulator arm 500 of FIG. 5). The degrees of freedom of input device 700 includes kinematic degrees of freedom defined by joints of input device 700, used to control the kinematics of manipulator arm 500, and may also include actuation degrees of freedom used to actuate a tool (e.g., instrument 511) connected to manipulator arm 500. Input device 700, like a tool of manipulator arm 500, may also be considered to have an end effector (or, more generally, a control frame) associated therewith, which itself has a number of kinematic degrees of freedom.

In some embodiments, input device 700 may have a sufficient number of degrees of freedom to fully control the position of an end effector. For example, the input device 700 may have six degrees of freedom that may independently control the three translation and three orientation degrees of freedom of an end effector of the instrument 511. In some cases, even though the input device 700 has such a sufficient number of degrees of freedom, the manipulator assembly (e.g., manipulator arm 500) has a number of degrees of freedom that is insufficient to independently control the three translation and three orientation degrees of freedom of the end effector. For example, the manipulator arm 500 may have only five degrees of freedom.

In some embodiments, the input device 700 may have additional degrees of freedom, which may be degrees of freedom operable to control the position of the end effector (e.g., a redundant degree of freedom), and/or may be degrees of freedom operable to actuate the instrument 26 (e.g., turning on or off suction or irrigation, actuating a clamp, engaging a staple with tissue, etc.). An input device having additional degrees of freedom is described in commonly-owned U.S. application Ser. No. 10/121,283, filed Apr. 11, 2002, entitled "Master Having Redundant Degrees of Freedom," the disclosure of which is incorporated herein by reference in its entirety. Further, in at least one embodiment, the instrument 511, either alone or in combination with a manipulator arm 500, may have additional kinematic degrees of freedom that add to the degrees of freedom of the manipulator arm 500. For example, the instrument 511 may have joints for controlling the position of the end effector. In some cases, even when combining the kinematic degrees of freedom of the manipulator arm 500 with the kinematic degrees of freedom of the instrument, the position of the end effector may not be fully controlled. This may be, e.g., due to the joints of the instrument 511 merely adding kinematic degrees of freedom that are redundant to those already provided by the manipulator arm 500. In some embodiments, the instrument 511 may have additional actuation degrees of freedom for actuating the instrument 511 (e.g., turning on or off suction or irrigation, actuating a clamp, engaging a staple with tissue, etc.).

To facilitate control of the instrument 511, the master control input device 700 may include one or more actuators or motors and, in some embodiments, sensors for each of a plurality of joints of the master control input device 700. The motors and sensors of the input device 700 may be operatively linked to the motors and sensors associated with the manipulator arms (e.g., arm 500 of FIG. 5) and the surgical instruments mounted thereon (e.g., instrument 511 of FIG. 5) via a control system disposed in, e.g., the surgeon's console 16, the electronics cart 24, and/or the patient cart 22, and/or any other element of MIRS system 10 (FIG. 1). The control system may include one or more processors for effecting control between the master control device input and responsive robotic arm and surgical instrument output and for effecting control between robotic arm and surgical instrument input and responsive master control output in the case of, e.g., force feedback.

Figure 7B:
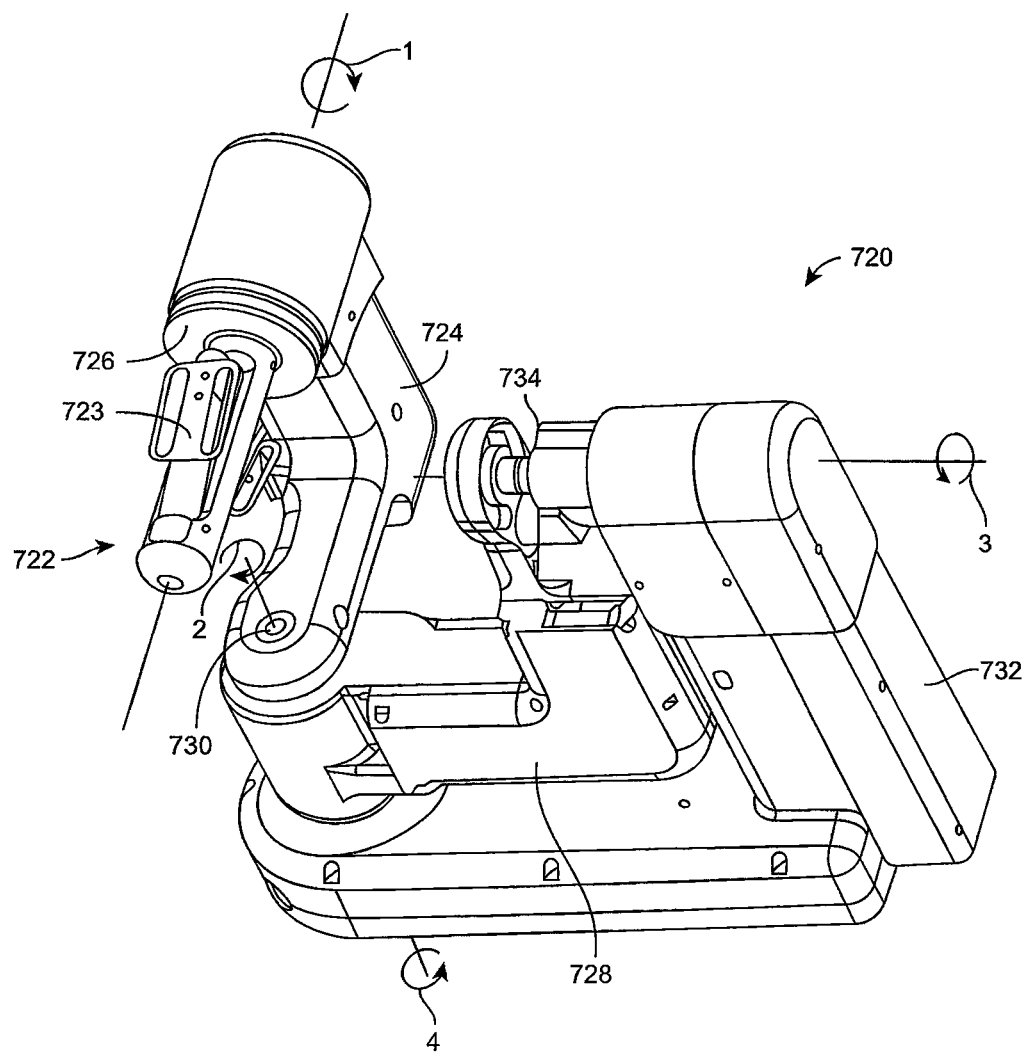
FIG. 7B is a perspective view of a gimbal or wrist of the input device of FIG. 7A.

FIG. 7B is a perspective view of a gimbal or wrist 720 according to an embodiment. According to this embodiment, gimbal or wrist 720 allows rotation of an actuatable handle 722 about three axes, axis 1, axis 2, and axis 3. More specifically, the handle 722 is coupled to a first elbow-shaped link 724 by a first pivotal joint 726. The first link 724 is coupled to a second elbow-shaped link 728 by a second pivotal joint 730. The second link 728 is pivotally coupled to a third elbow-shaped link 732 by a third pivotal joint 734. The gimbal or wrist 720 may be mounted on an articulated arm 740 (as shown in FIG. 7A) at axis 4 such that the gimbal or wrist 720 can displace angularly about axis 4. By way of such links and joints, the gimbal or wrist 720 may provide a number of kinematic degrees of freedom for the control input device 700 and be operable to control one or more of the end effector degrees of freedom.

In some embodiments, the handle 722 may include a pair of grip members 723 for actuating a tool or end effector. For example, by opening or closing the grip members 723, the jaw 608 of the end effector 606 (FIG. 6) may similarly be opened or closed. In other embodiments, one or more input elements of the handle 722 and/or of other elements of the surgeon's console 16 may be operable to actuate one or more degrees of freedom of the instrument 511 other than degrees of freedom for controlling the position of the instrument 26. For example, the surgeon's console 16 may include a foot pedal coupled to the control system for activating and deactivating a vacuum pressure.

In some embodiments, the joints of the gimbal or wrist 720 may be operatively connected to actuators, e.g., electric motors, or the like, to provide for, e.g., force feedback, gravity compensation, and/or the like. Furthermore, sensors such as encoders, potentiometers, and the like, may be positioned on or proximate to each joint of the gimbal or wrist 720, so as to enable joint positions of the gimbal or wrist 720 to be determined by the control system.

Figure 7C:
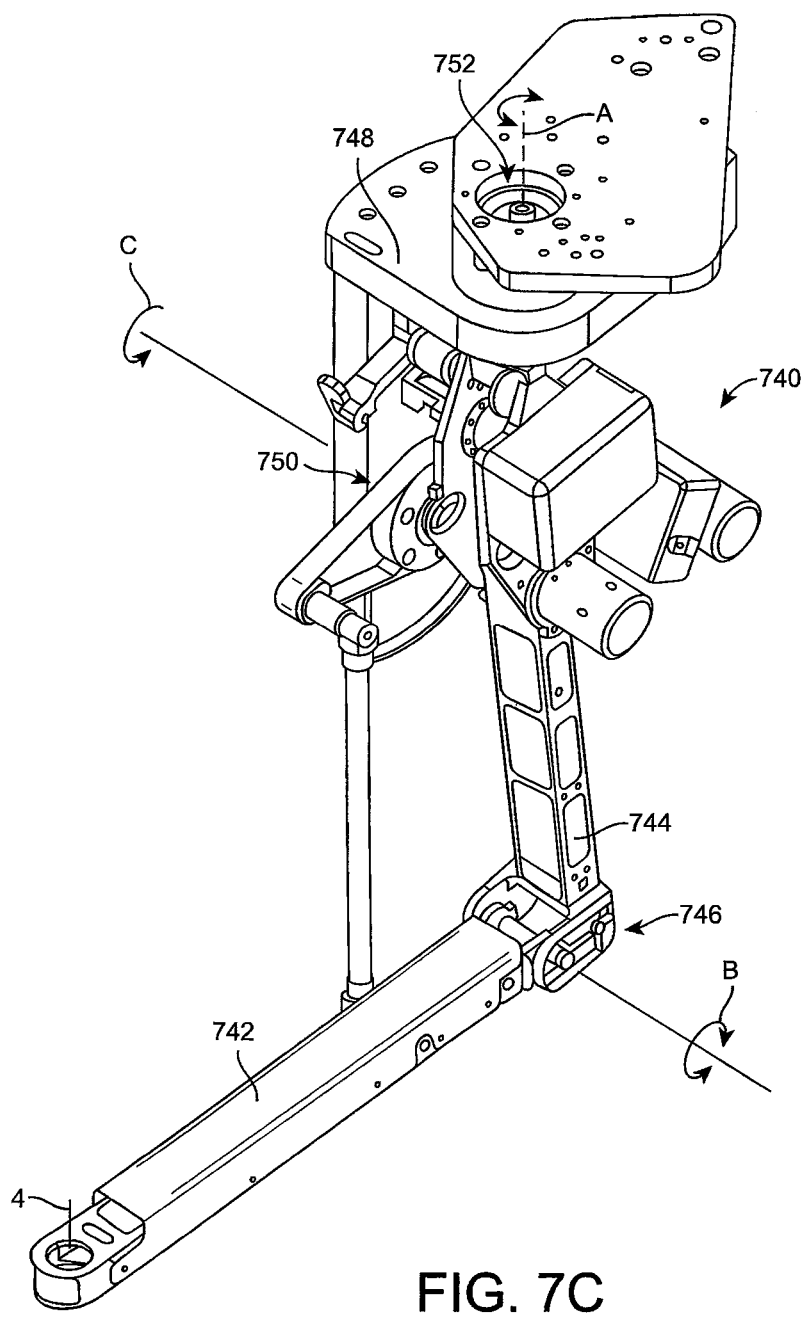
FIG. 7C is a perspective view of an articulated arm of the input device of FIG. 7A.

FIG. 7C is a perspective view of an articulated arm 740 according to an embodiment. According to this embodiment, the articulated arm 740 allows rotation of a gimbal or wrist 720 (FIG. 7B) about three axes, axis A, axis B, and axis C. More specifically, the gimbal or wrist 720 may be mounted on the arm 740 at axis 4 as previously described with reference to FIG. 7B. The gimbal or wrist 720 is coupled to a first link 742 which is pivotally coupled to a second link 744 by a first pivotal joint 746. The second link 744 is pivotally coupled to a third link 748 by a second pivotal joint 750. The third link 748 may be pivotally coupled to the surgeon's console 16 (FIG. 1) by a third pivotal joint 752. By way of such links and joints, the articulated arm 740 may provide a number of kinematic degrees of freedom for the control input device 700 and be operable to control one or more of the kinematic degrees of freedom of a manipulator assembly to thereby control the position of an instrument (e.g., instrument 511 of FIG. 5).

In some embodiments, the joints of the articulated arm 740 may be operatively connected to actuators, e.g., electric motors, or the like, to provide for, e.g., force feedback, gravity compensation, and/or the like. Furthermore, sensors such as encoders, potentiometers, and the like, may be positioned on or proximate to each joint of the articulated arm 740, so as to enable joint positions of the articulated arm 740 to be determined by the control system.

Input device 700 in certain embodiments is a device for receiving inputs from a surgeon or other operator and includes various components such as a gimbal or wrist 720 and an articulated arm 740. However, it will be appreciated by those of ordinary skill in the art that the input device could operate equally well by having fewer or a greater number of components than are illustrated in FIGS. 7A to 7C. Thus, the depiction of the input device 700 in FIGS. 7A to 7C should be taken as being illustrative in nature, and not limiting to the scope of the disclosure.

Figure 8:
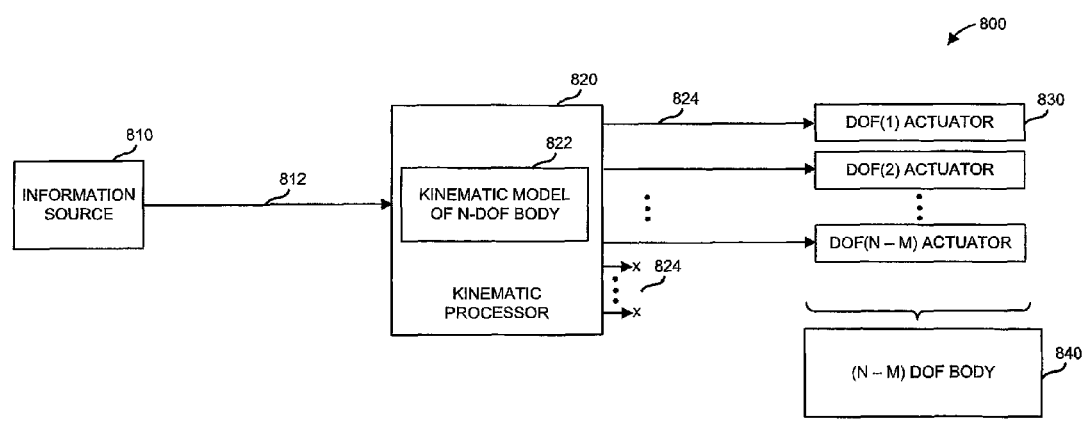
FIG. 8 is a block diagram showing a simplified system for controlling a mechanical body having fewer degrees of freedom than those mathematically modeled

FIG. 8 is a block diagram showing a simplified system 800 for controlling a mechanical body having fewer degrees of freedom than those mathematically modeled. The system 800 includes an information source 810, a kinematic processor 820 having a kinematic model 822, one or more actuators 830, and a mechanical body 840.

The information source 810 may be any suitable source of control information 812 for controlling a position of the mechanical body. In one embodiment, the information source 810 is an input device such as the surgeons console 16 (FIG. 1), the input control devices 36 (FIG. 2), and/or the master control input device 700 (FIGS. 7A to 7C). In such embodiments, the control information 812 may be a desired position of a mechanical body having N degrees of freedom. In one embodiment, the N degrees of freedom are those necessary to fully define the position of the mechanical body, i.e., three independently controllable translations and three independently controllable rotations. Accordingly, the output from the information source 810 may include parameters for fully controlling the position of the mechanical body. In one embodiment, the N degrees of freedom are insufficient to fully define the position of the mechanical body. For example, the N degrees are freedom are insufficient to independently control all three translations and three rotations of the mechanical body. Accordingly, the output from the information source 810 may include parameters insufficient to fully control the position of the mechanical body. In yet another embodiment, the N degrees of freedom may include one or more degrees of freedom that do not define the position of the mechanical body (i.e., non-kinematic degrees of freedom). For example, the N degrees of freedom may include one or more degrees of freedom for actuating an instrument such as actuating a vacuum pressure. Accordingly, the output from the information source 810 may include parameters for controlling non-kinematic characteristics of the mechanical body. These may not be limited to suction via a vacuum pressure, but may also or alternatively include irrigating, energizing (e.g., cauterizing), cutting (using, e.g., a single blade or multiple blades like scissors), and grasping (using, e.g., pincers, fingers, or the like).

In some embodiments, when the information source 810 is an input device, the input device itself also has N degrees of freedom, such that, at least in some cases, each degree of freedom of the input device may correspond to a degree of freedom of the mechanical body. For example, a roll of the input device may correspond to a desired roll of the mechanical body, or a pitch of the input device may correspond to a desired pitch of the mechanical body. In other embodiments, the input device may have a number of degrees of freedom greater than or fewer than the mechanical body. For example, the input device may have one or more redundant degrees of freedom, whereas the mechanical body may have no redundant degrees of freedom. For another example, the mechanical body may have one or more redundant degrees of freedom, whereas the input device may have no redundant degrees of freedom.

Although the input device provides an output indicating a desired position of a mechanical body having N degrees of freedom, the mechanical body 840 controlled by the input device lacks at least one of the necessary degrees of freedom for fully defining the position of the mechanical body. For example, the mechanical body 840 may lack a roll, yaw, and/or pitch degree of freedom, and/or may lack an up/down, left/right, and/or forward/backward translation degree of freedom. In the case where N represents the number of degrees of freedom for controlling a position of a mechanical body, and M represents the number of degrees of freedom regarding position that the mechanical body lacks, then in one embodiment the mechanical body may have N−M degrees of freedom. For example, N may be equal to six, corresponding to all three translations and all three rotations of a mechanical body, whereas M may represent one, corresponding to the roll of the mechanical body. However, in other embodiments, the mechanical body may have Nor even greater than N degrees of freedom, such as where the mechanical body includes redundant degrees of freedom, but still lacks at least one degree of freedom necessary to fully define the position of the mechanical body.

In other embodiments, the information source 810 is not an input device like a surgeon's console, but rather is a tool position measuring device. In this case, the kinematic block 820 is not a controller, but is a joint position estimator. For example, the tool position measuring device may include an optical fiber that extends the length of tool assembly 26 to the free end of the tool assembly 26, an electromagnetic sensor arranged proximate the joints of the manipulator assembly, or other sensor or imaging device operable to measure a position of the joints of the manipulator assembly. In many embodiments, the tool position measuring device is small and light enough so as not to interfere with motion of the tool. In an embodiment where the tool position measuring device includes an optical fiber, the properties (e.g., the refractive index) of the optical fiber may be altered as a result of changes in joint positions. Some examples of fiber optic sensors are described in U.S. Pat. App. Pub. No. US2007/0156019 A1 (filed Jul. 20, 2006), entitled "Robotic Surgery System Including Position Sensors Using Fiber Bragg Gratings" by Larkin et al., and U.S. patent application Ser. No. 12/164,829

(filed Jun. 30, 2008) entitled "Fiber optic shape sensor" by Giuseppe M. Prisco, both of which are incorporated herein by reference in their entirety for all purposes. The tool position measuring device may then be operable to determine a position of the tip of the tool (e.g., the free end of tool assembly 26) based on the altered properties of the optical fiber. The tool position measuring device may further be operable to measure a position of the tool in a number of degrees of freedom. For example, the tool position measuring device may measure one, two, or three translational positions of the tool (e.g., x, y, z positions), and/or one, two or three orientational positions of the tool (e.g., pitch, yaw, roll). In at least one embodiment, the tool position measuring device may be inoperable to measure one or more degrees of freedom positions of the tool. For example, when the tool position measuring device includes an optical fiber and deduces a tip position based on changes to the properties of the optical fiber, the tool position measuring device may have difficulty determining a roll movement of the tool. In embodiments where the information source 810 is a tool position measuring device, control information 812 may be measurement information indicating a measured position of the degrees of freedom of the tool tip.

In some embodiments, the tool position measuring device may be operable to measure the position of a number of degrees of freedom of the tool less than, equal to, or greater than a number of degrees of freedom of the manipulator assembly. In many embodiments, as already described for information sources being input devices, the mechanical body may have N degrees of freedom that are insufficient to fully define the position of the mechanical body, may include non-kinematic degrees of freedom, may include redundant degrees of freedom, etc.

The output from the information source 810, regardless of whether the information source 810 is an input device or a tool position measuring device, is applied to a kinematic model 822 of an N degree of freedom mechanical body in the kinematic processor 820. The kinematic processor 820 may be provided in any suitable component of MIRS system 10 (FIG. 1), such as the surgeon's console 16, electronics cart 24, and/or patient side cart 22, tool assembly 26, manipulator assembly, and/or the control system discussed with reference to FIG. 7A.

In embodiments where the information source 810 is an input device, the kinematic model 822 may be a model of a mechanical body having N degrees of freedom that correspond to the N degrees of freedom for which a desired control is output from the input device. For example, the input device may output parameters for fully controlling the position of the mechanical body, such as parameters for controlling three translations and three rotations of the mechanical body. The kinematic model 822 may then be a kinematic model of a mechanical body having three translations and three rotations. In some embodiments, one or more degrees of freedom that do not define the position of the mechanical body may be modeled or otherwise controlled separate from the kinematic model 822. Regardless, in most embodiments, the kinematic model 822 includes a mathematical representation of the one or more degrees of freedom lacking in the mechanical body 840. For example, the mechanical body 840 may lack a degree of freedom for controlling a roll of the mechanical body 840. However, the kinematic model 822 may be of a mechanical body having a degree of freedom for controlling the roll of the mechanical body, and the input device 810 may output information indicating a desired control of the roll of the mechanical body.

In embodiments where the information source 810 is a tool position measuring device, the kinematic model 822 may be a model of a mechanical body for which joint estimates (i.e., estimates of the position of joints corresponding to the degrees of freedom of the mechanical body 840) are to be generated. For example, if a joint estimation technique is used in which the tool position measurement device can only provide N degrees of freedom measurement, then the kinematic model 822 may have at least N degrees of freedom, the mechanical body may have (N−M) degrees of freedom, etc. However, in other embodiments, the mechanical body may have greater than N degrees of freedom, the manipulator assembly may be logically separated into multiple parts in which each part has no more than N joints or kinematic degrees of freedom while the tool measurement tool device is used to measure the position and orientation at the end of each part.

As a result of applying the control information 812 from the information source 810 to the kinematic processor 820, one or more individual control outputs 824 may be generated by the kinematic processor 820 and communicated to one or more actuators 830 operable to affect control of one or more of the degrees of freedom of the mechanical body 840. The number of individual control outputs 824 generated and communicated to the actuators 830 is fewer than the total number of individual control outputs 824 that may be generated by the kinematic processor 820. That is, the individual control outputs 824 communicated to the actuators 830 do not include information for controlling the degree(s) of freedom that the mechanical body 840 lacks. For example, the kinematic model 822 may model a mechanical body having degrees of freedom for fully defining the position of the mechanical body, and may calculate outputs for controlling all of those degrees of freedom. However, only a subset of those calculated outputs are used, as the mechanical body actually controlled (i.e., mechanical body 840) does not have all of the degrees of freedom modeled by the kinematic model 822. Accordingly, the individual control outputs 824 communicated to the actuators 830 are only a subset of the possible instructions that may be generated using the kinematic model 822.

In embodiments where the information source 810 is an input device, the individual control outputs 824 may include information indicating the desired position of a degree of freedom of the mechanical body 840. For example, an individual control output 824 may indicate the desired position (e.g., angle) of a joint associated with one of the degrees of freedom of the mechanical body 840.

In embodiments where the information source 810 is a tool position measuring device, the individual control outputs 824 may include information indicating the actual position of a degree of freedom of the mechanical body 840. For example, an individual control output 824 may indicate the actual position (e.g., angle) of a joint associated with one of the degrees of freedom of the mechanical body 840.

The individual control outputs 824 are received by one or more actuators 830 for controlling at least some of the degrees of freedom of a mechanical body 840. For example, the actuators 830 may be electric motors or the like operable to actuate joints of the mechanical body 840, as previously discussed with reference to, e.g., FIG. 5. In accordance with one embodiment, each actuator is operable to control a corresponding degree of freedom of the mechanical body 840. However, in other embodiments, one actuator may be operable to control more than one or fewer than one degree of freedom of the mechanical body 840.

The mechanical body 840 may be any suitable mechanical body having at least one degree of freedom. For example, the mechanical body may be a robotic manipulator arm (e.g., manipulator arm 100 described with reference to FIG. 4 or manipulator arm 500 described with reference to FIG. 5) and/or surgical instrument (e.g., instrument 26 described with reference to FIG. 1A or instrument 511 described with reference to FIG. 5). In some embodiments, the mechanical body may include the kinematic aspects of both a manipulator arm and surgical instrument.

As previously described, various embodiments incorporate information source 810 being an input device such that kinematic processor 820 outputs desired positions of the joints of body 840, whereas other embodiments incorporate information source 810 being a tool position measuring device such that kinematic processor 820 outputs actual positions of the joints of body 840. In yet other embodiments, a system may include both an input device for providing desired positions to a kinematic model and controller (i.e., a type of kinematic processor) unique to the input device, and a tool position measuring device for providing tool tip position information to a kinematic model and an estimator (i.e., a type of kinematic processor) unique to the tool position measuring device. In such a case, the kinematic model used by the tool tip position measuring device may be different than the kinematic model used by the input device. Further, the outputs of each kinematic model, i.e., the desired position and actual position of the joints of the manipulator assembly may be used together to calculate the actual amount of torque to be applied to each joint motor. In embodiments where a tool position measuring device is not provided, the system may acquire estimated joint positions and combine those with the desired positions output when using the input device to generate torque amounts. Some of these further embodiments are described with reference to FIG. 9.

System 800 in certain embodiments is a simplified system for controlling a mechanical body and includes various components such as an input device 810, kinematic processor 820, actuator(s) 830, and mechanical body 840. However, it will be appreciated by those of ordinary skill in the art that the system could operate equally well by having fewer or a greater number of components than are illustrated in FIG. 8. Thus, the depiction of the system 800 in FIG. 8 should be taken as being illustrative in nature, and not limiting to the scope of the disclosure.

Figure 9:
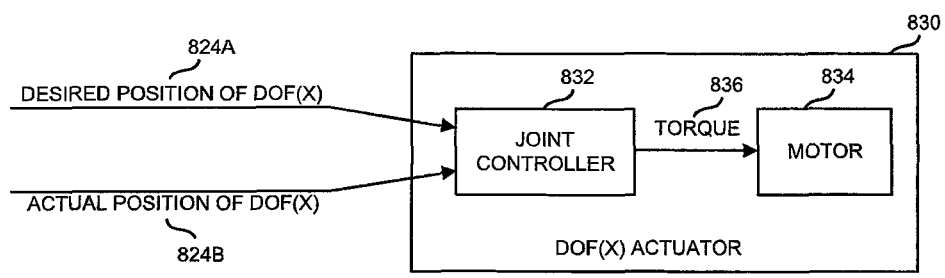
FIG. 9 is a block diagram of an actuator according an embodiment.

FIG. 9 is a block diagram of an actuator 830 according an embodiment. The actuator 830 includes a joint controller 832 and a motor 834, where the joint controller 832 is operable to generator a torque command 836 for controlling motor 834. The motor 834 may be coupled to one or more joints of a manipulator assembly for controlling the degrees of freedom of the manipulator assembly. In this embodiment, the actuator 830 is operable to control degree of freedom (X).

To generate a torque command 836, the joint controller 834 receives the desired position of the degree of freedom (X) 824A. The desired position may be received from an input device such as a surgeon's console. For example, the desired position 824A may be generated by the kinematic processor 820 (FIG. 8) when the information source 810 is an input device. Accordingly, the desired position 824A may be generated by applying control information communicated from the input device to the kinematic model 822, and using only one of a subset of the individual control outputs 824 as the desired position 824A.

To generate the torque command 836, the joint controller 834 also receives the actual position of the degree of freedom (X) 824B. The actual position may be generated using one or more of a number of techniques. In one embodiment, the actual position may be determined based on encoders used for each joint motor. In other embodiments, the actual position may be calculated from the position (e.g., location and/or orientation) of the end of the manipulator assembly (e.g., a tool tip) and applying inverse kinematics. A sensor device for sensing the position of the end of the manipulator assembly may include an optical fiber disposed along the length of the manipulator assembly with one end fixed at the tool tip such that changes in joint position cause changes to properties (e.g., refractive index) of the optical fiber. In another embodiment, the sensor device may include one or more electromagnetic sensors attached to the end point of the manipulator assembly such that any changes in the tip position could be measured from the electromagnetic field generator. For example, with reference to FIG. 8, the information source 810 may be a sensing device operable to determine the tool tip position, and by applying the tool tip position measurement to the kinematic model 822, one of a subset of the individual control output 824 may be used as the actual position 824B.

Upon receiving both the desired position and the actual position of DOF(X), the joint controller 832 may determine the appropriate amount of motor torque that will cause the degree of freedom to move from its actual (i.e., current) position to the desired position. The joint controller 832 then sends the torque command 836 indicating this amount of torque to the motor 834.

Figure 10A:
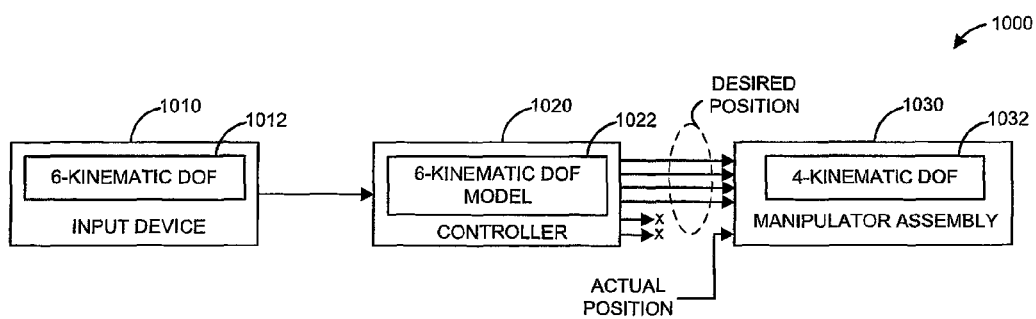
FIG. 10A is a block diagram showing a simplified system for controlling a manipulator assembly using an input device in accordance with a first embodiment.

FIG. 10A is a block diagram showing a simplified system 1000 for controlling a manipulator assembly using an input device in accordance with a first embodiment. System 1000 includes an input device 1010, a controller 1020, and a manipulator assembly 1030. The input device 1010 may be similar to the information source 810 discussed with reference to FIG. 8, controller 1020 may be similar to the kinematic processor 820 discussed with reference to FIG. 8, and the manipulator assembly 1030 may be similar to the actuators and mechanical body 840 discussed with reference to FIG. 8. In one embodiment, the manipulator assembly 1030 includes a manipulator (e.g., manipulator 500) and/or a tool (e.g., tool 511). Manipulator assembly 1030 may have one or more manipulator kinematic degrees of freedom and, in some embodiments, may also or alternatively have one or more actuation degrees of freedom. Further, manipulator assembly 1030 may be operable to control the position of one or more end effectors (or, more generally, control frames). For example, an end effector could be defined at a tip of a tool that is part of manipulator assembly 1030, part-way up a shaft of such a tool, etc. The end effector also has a number of degrees of freedom which may be the same as or different than the manipulator degrees of freedom.

In accordance with the embodiment depicted in FIG. 10A, the input device 1010 and controller 1020 are operable to control a greater number of kinematic manipulator degrees of freedom (i.e., degrees of freedom of manipulator assembly 1030) than the manipulator assembly 1030 actually has. For example, the input device 1010 may have six kinematic degrees of freedom 1012 including three independently controllable rotation degrees of freedom and three independently controllable translation degrees of freedom. The input device 1010 outputs parameters or other information corresponding to the position of the input device 1010 or otherwise indicating a desired position of an end effector associated with manipulator assembly 1030.

The output from the input device 1010 are received and processed by the controller 1020 to provide instructions for controlling the manipulator assembly 1030 (e.g., instructions for controlling motors associated with joints of manipulator assembly 1030). In this embodiment, the controller 1020 includes a kinematic model 1022 of a manipulator assembly having six kinematic degrees of freedom for controlling three independently controllable rotation and three independently controllable translation degrees of freedom of the end effector.

A subset of the results from applying the output from the input device 1010 to the kinematic model 1022 are then used to control the manipulator assembly 1030. For example, the subset of the results may be communicated to one or more actuators associated with joints of the manipulator assembly 1030. The manipulator assembly 1030 in this embodiment has four kinematic degrees of freedom. The manipulator assembly 1030 is thus lacking two kinematic degrees of freedom. For example, the manipulator assembly 1030 may lack degrees of freedom corresponding to yaw and pitch movements, or may lack degrees of freedom corresponding to two translational movements, etc. Accordingly, the subset includes instructions for controlling only those degrees of freedom that the manipulator assembly 1030 is configured to have. In this case, the instructions are indicative of a desired position of the joints of manipulator assembly 1030, and may be combined with information indicating the actual position of the joints of the manipulator assembly 1030. The combination may be used to determine the appropriate torque to apply to the joint motors.

In other embodiments, the input device and kinematic model may not have six kinematic degrees of freedom, and the end effector may not have four kinematic degrees of freedom. Rather, the input device and kinematic model may be configured to control a greater number of degrees of freedom than the manipulator assembly is equipped with. For example, the input device 1010 and controller 1020 may be configured to control five kinematic degrees of freedom, whereas the manipulator assembly may have anywhere from one to four kinematic degrees of freedom.

Figure 10B:
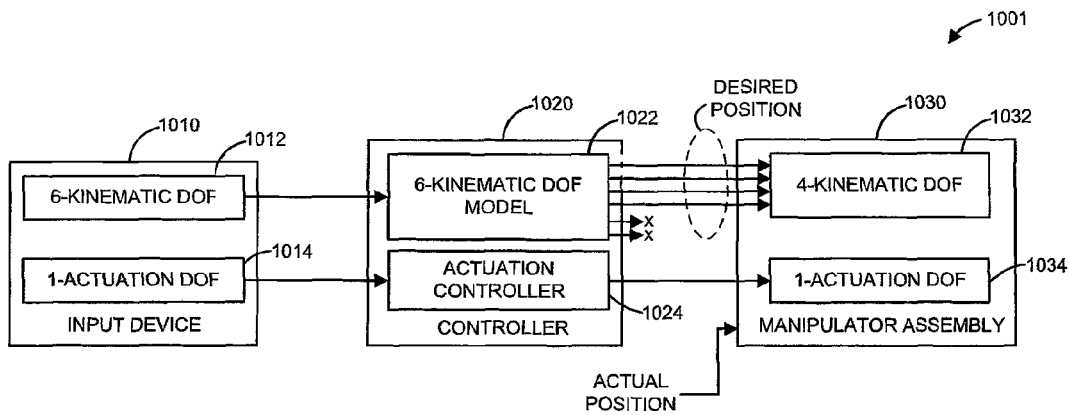
FIG. 10B is a block diagram showing a simplified system for controlling a manipulator assembly using an input device in accordance with a second embodiment.

FIG. 10B is a block diagram showing a simplified system 1001 for controlling a manipulator assembly using an input device in accordance with a second embodiment. System 1001 includes an input device 1010, a controller 1020, and a manipulator assembly 1030, which may be similar to those discussed with reference to FIG. 10A.

In accordance with this embodiment, the input device 1010 and controller 1020 are operable to control a greater number of kinematic degrees of freedom than the manipulator assembly 1030 has, similar to the embodiment discussed with reference to FIG. 10A. Further, the input device 1010 is operable to actuate a non-kinematic degree of freedom of the manipulator assembly 1030. For example, the input device 1010 may be operable to actuate a vacuum pressure associated with the manipulator assembly 1030.

Accordingly, in this embodiment, the input device 1010 includes six kinematic degrees of freedom 1012 as well as at least one actuation degree of freedom 1014, where the actuation degree of freedom refers to a non-kinematic degree of freedom. In one embodiment, the actuation degree of freedom may be actuated via an element on the input device 1010 such as one or more grip members 723 (FIG. 7B). The input device 1010, via the six kinematic degrees of freedom, may then output parameters or other information corresponding to the position of the input device 1010 or otherwise indicating a desired position of an end effector associated with the manipulator assembly 1030. Further, the input device 1010, via the one actuation degree of freedom, may output parameters or other information for actuating a functionality of the manipulator assembly 1030 or a tool coupled to or part of manipulator assembly 1030 (e.g., actuating a vacuum, one or more pincers/fingers, etc.).

The output from the input device 1010 are received and processed by the controller 1020 to provide instructions for controlling the manipulator assembly 1030. In this embodiment, the controller 1020 includes a kinematic model 1022 of a manipulator assembly having six kinematic degrees of freedom, similar to that described with reference to FIG. 10A. Further, the controller 1020 also includes an actuation controller 1024 which may be operable to process the output from the input device 1010 concerning the actuation degree of freedom 1014 and use this output to actuate a function of the manipulator assembly 1030.

A subset of the results from applying the output from the input device 1010 to the kinematic model 1022 are then used to control the manipulator assembly 1030, similar to that discussed with reference to FIG. 10A. Further, the results from applying the actuation output from the input device 1010 to the actuation controller 1024 may be used to control actuation of the manipulator assembly 1030 (or actuation of a tool coupled to or part of manipulator assembly 1030). As discussed with reference to FIG. 10A, in other embodiments, the input device and kinematic model may not have six kinematic degrees of freedom, and the end effector may not have four kinematic degrees of freedom. Further, in some embodiments, the input device 1010 may include a plurality of actuation degrees of freedom, the actuation controller 1024 may be operable to process the output for a plurality of actuation degrees of freedom from the input device 1010, and the manipulator assembly 1030 may have a corresponding number of actuation degrees of freedom that may be controlled by the input device 1010 separate from the control of the manipulator assembly 1030.

Figure 10C:
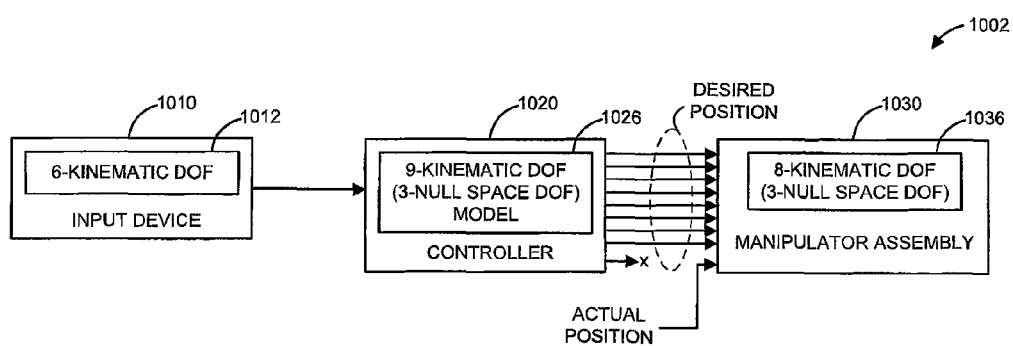
FIG. 10C is a block diagram showing a simplified system for controlling a manipulator assembly using an input device in accordance with a third embodiment.

FIG. 10C is a block diagram showing a simplified system 1002 for controlling a manipulator assembly using an input device in accordance with a third embodiment. System 1002 includes an input device 1010, a controller 1020, and a manipulator assembly 1030, which may be similar to those discussed with reference to FIG. 10A.

In accordance with this embodiment, the manipulator assembly 1030 has a number of kinematic degrees of freedom (e.g., eight), which includes at least one null space degree of freedom (e.g., three null space degrees of freedom), but still lacks at least one of the degrees of freedom necessary to fully define the position of an end effector associated with the manipulator assembly 1030. For example, although the manipulator assembly 1030 includes eight kinematic degrees of freedom including redundant degrees of freedom, it still lacks at least one independently controllable rotation or translation degree of freedom.

It should be recognized that when null space degrees of freedom of a manipulator assembly are described herein, it is assumed that the control frame is located on the manipulator assembly (e.g., the control frame is located at a tool tip). However, embodiments are not limited to such cases, and thus where null space degrees of freedom of a manipulator assembly are described, embodiments alternatively include null space degrees of freedom of a Jacobian, where the Jacobian is associated with the manipulator assembly and a control frame having an arbitrarily defined location, such as at a tissue of a patient, at a fixed distance from the tool tip, etc.

The input device 1010 includes six kinematic degrees of freedom 1012 similar to those discussed with reference to FIG. 10A. The controller 1020 is then operable to process the output from the input device 1010 by applying the output to a kinematic model 1026 including nine kinematic degrees of freedom, which includes six kinematic degrees of freedom such as those discussed with reference to FIG. 10A as well as three null space degrees of freedom. The controller 1020 may thus generate outputs on the assumption that the manipulator assembly 1030 includes nine kinematic degrees of freedom that include three null space degrees of freedom. However, since the manipulator assembly 1030 only includes eight kinematic degrees of freedom, the controller 1020 does not provide an output corresponding to the missing kinematic degree of freedom of the manipulator assembly 1030. Rather, the controller 1020 outputs instructions for controlling the eight kinematic degrees of freedom of the manipulator assembly 1030.

Figure 10D:
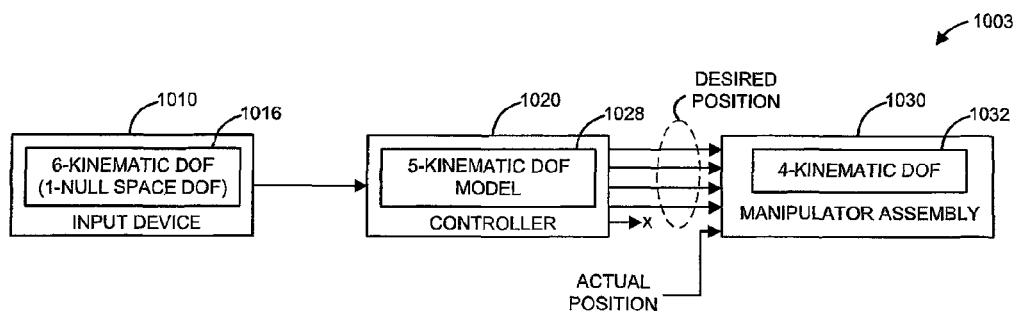
FIG. 10D is a block diagram showing a simplified system for controlling a manipulator assembly using an input device in accordance with a fourth embodiment.

FIG. 10D is a block diagram showing a simplified system 1003 for controlling a manipulator assembly using an input device in accordance with a fourth embodiment. System 1003 includes an input device 1010, a controller 1020, and a manipulator assembly 1030, which may be similar to those discussed with reference to FIG. 10A.

In accordance with this embodiment, the input device 1010 includes one or more null space degrees of freedom, whereas the manipulator assembly 1030 does not include any null space degrees of freedom and includes fewer kinematic degrees of freedom than the input device 1010. In other embodiments, the manipulator assembly 1030 may also include the same or greater number of null space degrees of freedom as the input device 1010.

Accordingly, in this embodiment, the input device 1010 includes a number of degrees of freedom 1016 including seven kinematic degrees of freedom which include one null space degree of freedom. The output from the input device 1010 may then be processed and eventually fed into the controller 1020, where the controller 1020 includes a kinematic model of a manipulator assembly having five degrees of freedom. The controller 1020 may then apply the output from the input device 1010 to the kinematic model 1028, and then use a subset of the results to control the manipulator assembly 1030, similar to that discussed with reference to FIG. 10A.

In this embodiment, the manipulator assembly 1030 includes four kinematic degrees of freedom 1032. However, in other embodiments, the manipulator assembly 1030 may have fewer than four kinematic degrees of freedom. Further, while the input device 1010 is described as having one null space degree of freedom, the input device 1010 may have more than one null space degree of freedom. For example, the input device 1010 may have two, three, or four null space degrees of freedom.

Systems 1000, 1001, 1002, and 1003 in certain embodiments are simplified systems for controlling an end effector using an input device and include various components such as an input device 1010, controller 1020, and manipulator assembly 1030. However, it will be appreciated by those of ordinary skill in the art that the systems could operate equally well by having fewer or a greater number of components than are illustrated in FIGS. 10A to 10D. For example, in some embodiments, input devices may have both null space degrees of freedom and actuation degrees of freedom, in addition to one or more kinematic degrees of freedom, controllers may have both null space degrees of freedom and an actuation controller, and manipulator assemblies may have both null space degrees of freedom and actuation degrees of freedom. Thus, the depiction of the systems in FIGS. 10A to 10D should be taken as being illustrative in nature, and not limiting to the scope of the disclosure.

Figure 11A:
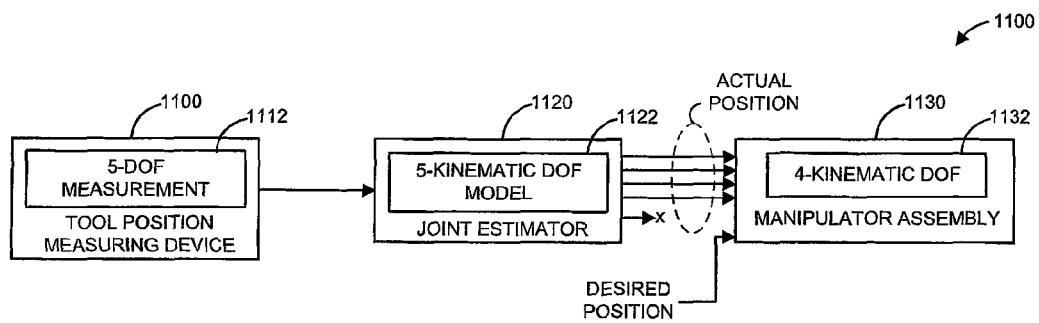
FIG. 11A is a block diagram showing a simplified system for controlling a manipulator assembly using a tool position measuring device in accordance with a first embodiment.

FIG. 11A is a block diagram showing a simplified system 1100 for controlling a manipulator assembly using a tool position measuring device in accordance with a first embodiment. System 1100 includes a tool position measuring device 1110, a joint estimator 1120, and a manipulator assembly 1130.

The elements of system 1100 are similar to the similarly labeled elements of system 1000, except that a tool position measuring device 1110 is provided instead of an input device 1010, and a joint estimator 1120 is provided instead of a controller. Accordingly, the description with reference to system 1000 is equally applicable to system 1100, except in the case of system 1100 instead of the controller receiving and applying desired position information, the controller receives and applies position measurement information. And, instead of generating desired positions, the joint estimator 1120 generates actual positions (e.g., joint angles) of the manipulator assembly joints. In some embodiments, the actual positions may be combined with information indicating the desired position of the joints of the manipulator assembly 1130. The combination may be used to determine the appropriate torque to apply to the joint motors.

Further, the tool position measuring device 1100 may only measure five degrees of freedom or less. In this particular embodiment, the tool position measuring device 1100 is illustrated as measuring five degrees of freedom, however, it may similarly measure four degrees of freedom, three degrees of freedom, or less than three degrees of freedom. And, the joint estimator 1120 uses only a 5-kinematic DOF model 1122 which generates only five joint positions, four of which are used (as they correspond to actual joints of the manipulator assembly 1130) and one of which is discarded (as there is no corresponding joint in the manipulator assembly 1130). In some embodiments, a 6-kinematic DOF model 1122 could be used in which two joint estimates would then be discarded, or fewer than five kinematic DOF could be used.

Figure 11B:
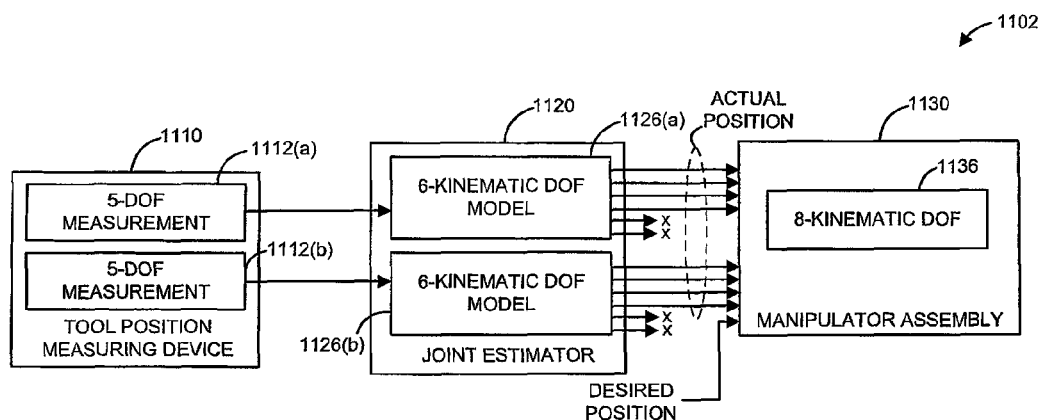
FIG. 11B is a block diagram showing a simplified system for controlling a manipulator assembly using a tool position measuring device in accordance with a second embodiment.

FIG. 11B is a block diagram showing a simplified system 1102 for controlling a manipulator assembly using a tool position measuring device in accordance with a second embodiment. System 1102 includes a tool position measuring device 1110, a joint estimator 1120, and a manipulator assembly 1130.

The elements of system 1102 are similar to the similarly labeled elements of system 1002, except that a tool position measuring device 1110 is provided instead of an input device 1010, and a joint estimator 1120 is provided instead of a controller. Accordingly, the description with reference to system 1002 is equally applicable to system 1102, except in the case of system 1102 instead of the controller receiving and applying desired position information the joint estimator receives and applies position measurement information. And, instead of generating desired positions, the joint estimator 1120 generates actual positions (e.g., joint angles) of the manipulator assembly joints. In some embodiments, the actual positions may be combined with information indicating the desired position of the joints of the manipulator assembly 1130. The combination may be used to determine the appropriate torque to apply to the joint motors.

Further, in this particular embodiment, the manipulator assembly is shown as having eight kinematic degrees of freedom with multiple pitch and yaw joints. For some embodiments of manipulator assemblies, the manipulator assembly may be logically separated into multiple parts. In the embodiments where optical fiber is used to measure the position and orientation at the end of each part, each part has five or fewer joints or degrees of freedom as the tool position measuring device 1112(a) or 1112(b) measures five degrees of freedom. The parts may each have the same or different number of degrees of freedom. For example, in this embodiment, the manipulator assembly is logically separated into two parts each having four degrees of freedom.

In at least one embodiment, the number of joints in each part may be maximized prior to incorporating joints into other parts. For example, for a manipulator assembly having seven degrees of freedom, one part may have five degrees of freedom (i.e., the maximum number) and another part may have the remaining degrees of freedom, i.e., two degrees of freedom. For another example, for a manipulator assembly having twelve degrees of freedom, two parts may each have five degrees of freedom, while a third part has only two degrees of freedom. In some cases, joint angles for one or more parts may be computed using geometries rather than inverse kinematics, where it is more computationally efficient to do so. For example, it may be more computationally efficient to use geometries over inverse kinematics when calculating joint estimations for a part having a number of degrees of freedom equal to or less than two.

The tool position measuring device 1110 may be operable to measure a position for each logical part of the manipulator assembly. For example, the tool position measuring device 1110 may measure a tip position of the first part and a tip position of the second part. The tip position of each part may be measured in the same or different number of degrees of freedom, where the measured degrees of freedom may be less than, the same, or greater than the degrees of freedom of the corresponding part. In this particular example, the tip position of the first part is measured in five degrees of freedom 1112(*a*), and the tip position of the second part is similarly measured in five degrees of freedom 1112(*b*). It should be recognized that these need not be the same, and in some embodiments may be any number less than five.

The joint estimator 1120 may then include a kinematic model for each logical part of the manipulator assembly. In this embodiment, joint estimator 1120 includes a first kinematic model 1126(*a*) and a second kinematic model 1126(*b*). The first kinematic model 1126(*a*) is a kinematic model of the first part of the manipulator assembly 1130, and the second kinematic model 1126(*b*) is a kinematic model of the second part of the manipulator assembly 1130. Each kinematic model receives the output from the tip measurement corresponding to its respective manipulator assembly part. For example, the output of the first measurement 1112(*a*) is applied to the first kinematic model 1126(*a*), and the output of the second measurement 1112(*b*) is applied to the second kinematic model 1126(*b*). The first kinematic model 1126(*a*) then outputs the actual position of the first part of the manipulator assembly 1130, whereas the second kinematic model 1126(*b*) outputs the actual position of the second part of the manipulator assembly 1130.

It should be apparent that the degrees of freedom of at least one of the kinematic models 1126(*a*) and 1126(*b*) may be greater than the actual number of degrees of freedom of the corresponding manipulator assembly part. In this particular embodiment, although not necessary, both kinematic models have a greater number of degrees of freedom than their corresponding manipulator assembly part. That is, the first kinematic model 1126(*a*) has five degrees of freedom whereas the first part of manipulator assembly 1130 only has four degrees of freedom, and likewise for the second kinematic model 1126(*b*) and second part of manipulator assembly 1130. This extra degree of freedom is used to generate an output but, similar to other extra kinematic model degrees of freedom described herein, is not subsequently used to determine the actual position of the manipulator assembly parts.

It should be recognized that while the systems described with reference to FIGS. 11A and 11B are considered similar for purposes of description, the embodiments described with reference to FIGS. 10A to 10D are directed to systems for generating desired positions of manipulator assembly joints, whereas the embodiments described herein with reference to FIGS. 11A and 11B are directed to systems for generating actual positions of manipulator assembly joints. In some embodiments and as already described, these systems may be combined into one system. For example, the input device and controller of FIGS. 10A to 10D may be used to generate a desired position, the tool position measuring device and joint estimator of FIGS. 11A and 11B may be used to generate an actual position, and these generated positions may be used in combination as described with reference to FIG. 9.

Figure 12A:
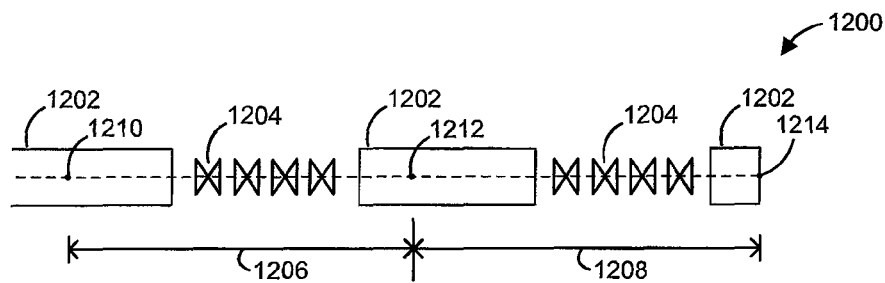
FIG. 12A is a manipulator assembly having more than five degrees of freedom according to an embodiment.

FIG. 12A is a manipulator assembly 1200 according to an embodiment. Manipulator assembly 1200 may be similar to manipulator assembly 1130 described with reference to FIG. 11B. Manipulator assembly 1200 includes a number of links 1202 and a number of joints 1204. The manipulator assembly 1200 is logically separated into a first part 1206 and a second part 1208. The first part 1206 extends from a point on the manipulator assembly, farthest from the free end of the manipulator assembly, that is defined as the base 1210. The first part 1206 extends from the base 1210 to a point within the manipulator assembly identified as the tip position of the first part 1212. The second part 1208 then extends from the tip position of the first part 1212 to a point defined as the tip position of the second part 1214 which, in this example, is located at the free end of the manipulator assembly 1200.

A number of joints are located within the first part 1206 and a number of different joints are located within the second part 1208. The number may not be the same, but in this example each of the first and second part include four joints. In other examples, where the total number of joints is eight, the first and second parts may respectively include five and three, or three and five joints. Various other combinations for manipulator assemblies having more than five joints may also be implemented. Further, the manipulator assembly may be logically separated into more than two parts. For example, when the total number of joints is eight, a first part may have five joints, a second part may have two joints, and a third part may have one joint. In most embodiments, when a joint estimation technique is used in which the tool position measurement device can only provide N degrees of freedom measurement, then each part includes no more than N joints or degrees of freedom. Further, when a manipulator assembly includes more than N kinematic degrees of freedom, those degrees of freedom are separated into multiple logical parts. In one embodiment, where a fiber optic approach is used in which estimation of the roll orientation is not available, then each part may include no more than five joints or kinematic degrees of freedom.

Figure 12B:
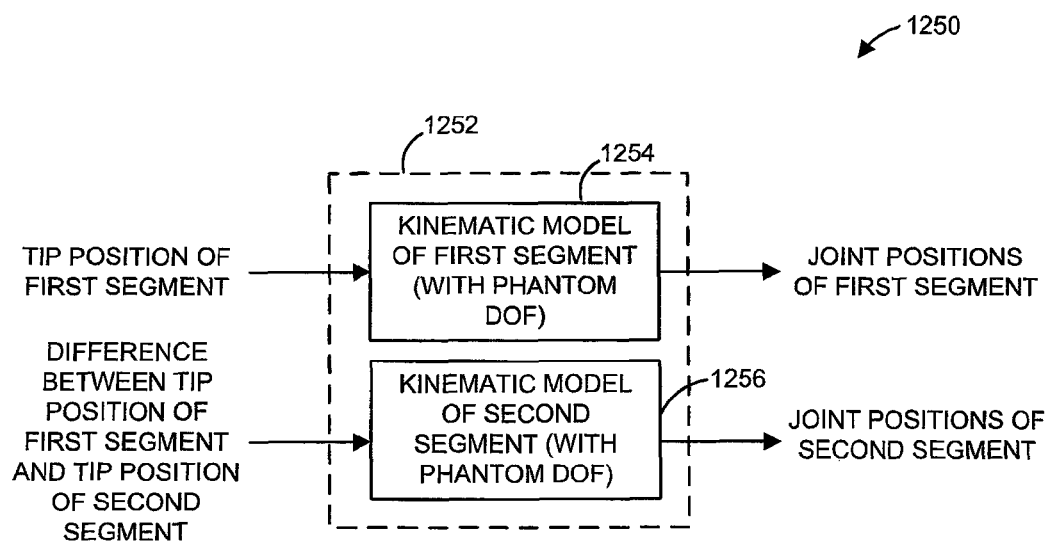
FIG. 12B depicts a block diagram illustrating the calculation of joint positions of multiple manipulator assembly parts according to an embodiment.

Turning briefly to FIG. 12B, FIG. 12B depicts a block diagram 1250 illustrating the calculation of joint positions of multiple manipulator assembly parts according to an embodiment. A joint estimator 1252 in this example includes a first kinematic model 1254 and a second kinematic model 1256. The first kinematic model 1254 is a kinematic model of the first segment or part of the manipulator assembly. For example, this may be a kinematic model of first part 1206. The second kinematic model 1256 is a kinematic model of the second segment or part of the manipulator assembly. For example, this may be a kinematic model of second part 1208.

Each of the kinematic models includes a phantom degree of freedom; that is, a degree of freedom that does not exist in the corresponding part of the manipulator assembly. For example, in the embodiment depicted in FIG. 12A, each of the kinematic models may include a phantom roll degree of freedom as the estimation of the roll orientation may not be available when using the fiber optic approach. In other embodiments, however, one or more of the kinematic models may include more than one phantom degree of freedom. In some embodiments, only one kinematic model includes a phantom degree of freedom.

The tip position of the first segment is input into the first kinematic model 1254. For example, the tip position 1212 may be input into first kinematic model 1254. The output from first kinematic model 1254 is the joint positions of first segment 1206 (as well as one set of outputs, corresponding to the phantom degree of freedom, that can be ignored). The difference between the tip position of the first segment (e.g., tip position 1212) and the tip position of the second segment (e.g., tip position 1214) is input into the second kinematic model 1256. The output from second kinematic model 1256 is the joint positions of second segment 1208 (as well as one set of outputs, corresponding to the phantom degree of freedom, that can be ignored).

Figure 13:
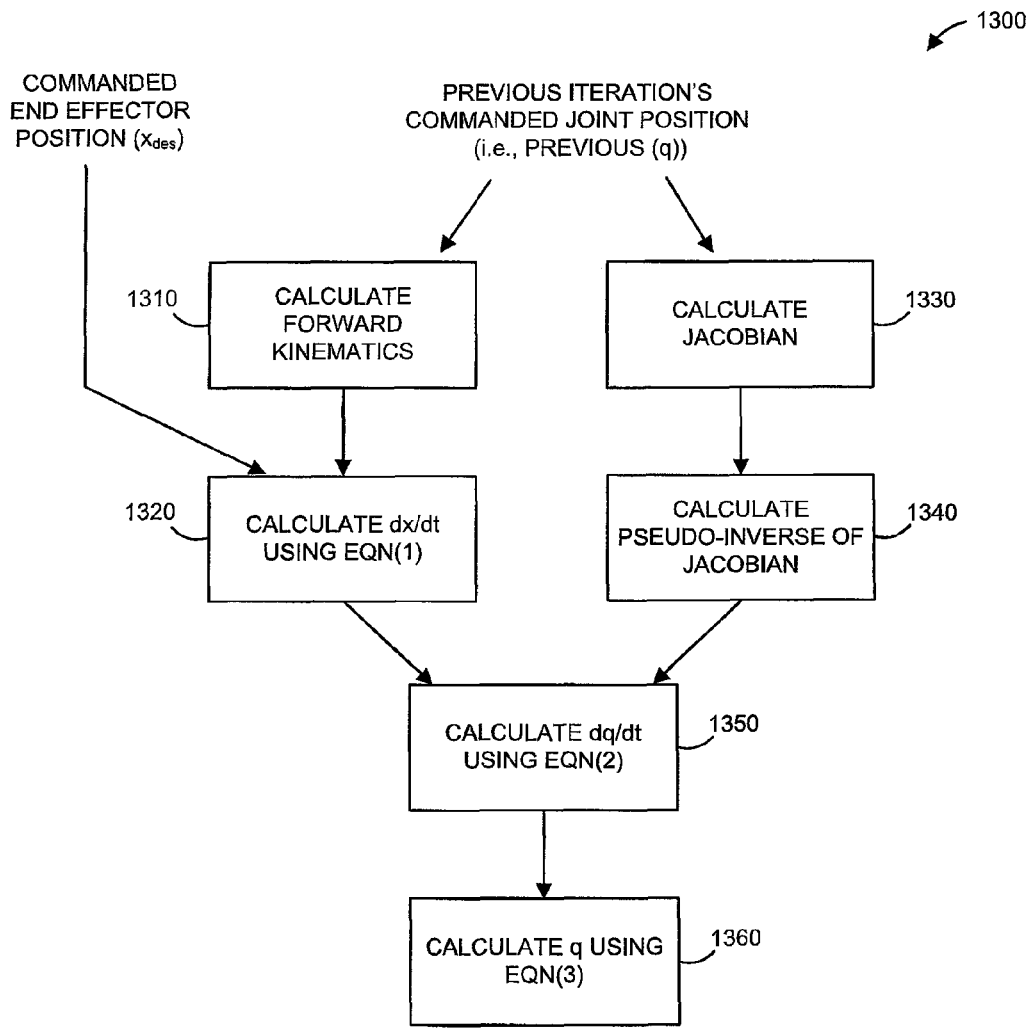
FIG. 13 is a flowchart showing a process for controlling manipulator arms, tools, and/or end effectors using an input device according to a first embodiment.

FIG. 13 is a flowchart showing a process 1300 for controlling manipulator arms, tools, and/or end effectors using an input device according to a first embodiment. The manipulator arms, tools, and/or end effectors may be any of those described herein, such as manipulator arms 100 (FIG. 4), manipulator arms 500 (FIG. 5), tools 26 (FIG. 1A), surgical tool 600 (FIG. 6A), endoscope 620 (FIG. 6B), overtube 630 (FIG. 6C), actuators 830 and/or mechanical body 840 (FIG. 8), etc. The input device may be any of the input devices described herein, such as input device 36 (FIG. 2), input device 700 (FIGS. 7A to 7C), input device 810 (FIG. 8), etc. Further, the process 1000 may be performed by any of the controllers described herein, such as the control system discussed with reference to FIG. 7A, kinematic processor 820 (FIG. 8), and/or any other suitable controller provided in any suitable component of MIRS system 10 (FIG. 1), such as the surgeon's console 16, electronics cart 24, and/or patient side cart 22.

In one particular embodiment, kinematic degrees of freedom of a manipulator assembly may be controlled by driving one or more joints via the controller using motors of the system, the joints being driven according to coordinated joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator assembly has degrees of freedom, and in some exemplary embodiments, the joint space may have more dimensions than the manipulator assembly has degrees of freedom as the manipulator assembly may lack at least one degree of freedom necessary to fully define the position of an end effector associated with the manipulator assembly. Further, a particular configuration of the manipulator assembly may represent a particular point in the joint space, with each coordinate corresponding to a joint state of an associated joint of the manipulator assembly where an associated joint of the manipulator exists.

In an exemplary embodiment, the system includes a controller in which a commanded position and velocity of a feature in the work-space, denoted here as its Cartesian space, are inputs. The feature may be any feature on the manipulator assembly or off the manipulator assembly which can be used as a control frame to be articulated using control inputs. An example of a feature on the manipulator assembly, used in many examples described herein, would be the tool-tip. Another example of a feature on the manipulator assembly would be a physical feature which is not on the tool-tip, but is a part of the manipulator assembly, such as a pin or a painted pattern. An example of a feature off the manipulator assembly would be a reference point in empty space which is exactly a certain distance and angle away from the tool-tip. Another example of a feature off the manipulator assembly would be a target tissue whose position relative to the manipulator assembly can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints of the manipulator assembly. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J\,dq/dt$$

Thus, even when there is no closed-form mapping between input and output positions, mappings of the velocities can iteratively be used, such as in a Jacobian-based controller, to implement a movement of the manipulator from a commanded user input. However, a variety of implementations can be used. Although many embodiments include a Jacobian-based controller, some implementations may use a variety of controllers that may be configured to access the Jacobian to provide any of the features described herein.

One such implementation is described in simplified terms below. The commanded joint position is used to calculate the Jacobian (J). Each time step (Δt) calculates a Cartesian space velocity (dx/dt) to perform the desired move ($dx_{des}/dt$) and to correct for built up deviation (Δx) from the desired Cartesian space position. This Cartesian space velocity is then converted into a joint-space velocity (dq/dt) using the pseudo-inverse of the Jacobian ($J^{\#}$). The resulting joint-space commanded velocity is then integrated to produce joint-space commanded position (q). These relationships are listed below:

$$dx/dt = dx_{des}/dt + k\Delta x \qquad (1)$$

$$dq/dt = J^{\#} dx/dt \qquad (2)$$

$$q_i = q_{i-1} + dq/dt\,\Delta t \qquad (3)$$

The pseudo-inverse of the Jacobian (J#) directly maps the desired tool tip motion (and, in some cases, a remote center of pivotal tool motion) into the joint velocity space. If the manipulator assembly being used has more useful joint axes than tool tip (i.e., end effector) degrees of freedom (up to six), (and when a remote center of tool motion is in use, the manipulator assembly should have an additional 3 joint axes for the 3 degrees of freedom associated with location of the remote center), then the manipulator assembly is said to be redundant. A Jacobian associated with a redundant manipulator assembly includes a "null-space" having a dimension of at least one. In this context, the "null-space" of the Jacobian (N(J)) is the space of joint velocities which instantaneously achieves no tool tip motion (and when a remote center is used, no movement of the pivotal point location), and "null-motion" is the path of joint positions which also produces no instantaneous movement of the tool tip and/or location of the remote center. Incorporating or injecting the calculated null-space velocities into the control system of the manipulator assembly to achieve the desired reconfiguration of the manipulator assembly (including any reconfigurations described herein) changes above equation (2) to the following:

$$dq/dt = dq_{perp}/dt + dq_{null}/dt \qquad (4)$$

$$dq_{perp}/dt = J^{\#}dx/dt \qquad (5)$$

$$dq_{null}/dt = (I - J^{\#}J)z = V_n V_n^T z = V_n \alpha \qquad (6)$$

The joint velocity according to Equation (4) has two components: the first being the null-perpendicular-space component, the "purest" joint velocity (shortest vector length) which produces the desired tool tip motion (and when the remote center is used, the desired remote center motion); and the second being the null-space component. Equations (2) and (5) show that without a null-space component, the same equation is achieved. Equation (6) starts with a traditional form for the null-space component on the left, and on the far right side, shows the form used in an exemplary system, wherein $(V_n)$ is the set of orthonormal basis vectors for the null-space, and $(\alpha)$ are the coefficients for blending those basis vectors. In some embodiments, $\alpha$ is determined by knobs that are used to shape the motion within the null-space as desired.

As previously mentioned, fully controlling the position of a rigid body requires six independently controllable degrees of freedom, three for translations and three for orientations. This lends itself nicely to a Jacobian based control algorithm, such as that discussed above, in which a 6×N Jacobian matrix is used. However, some rigid bodies lack at least one of these degrees of freedom. For example, a rigid endoscope tip without an articulating wrist is missing two degrees of freedom at the wrist, specifically wrist pitch and yaw. So it only has four degrees of freedom at the tip. This creates a problem for the 6×N Jacobian approach, because the problem is now over-constrained. Using the 6×N Jacobian based controller, when the endoscope tip is commanded to either pan or tilt, since it has a non-wristed tip, it can only do one thing, and this is to do a combination of both. This results in a sluggish unresponsive feel which is undesirable. Accordingly, not only is it desirable to obviate this unresponsive feel, it is also desirable to use a 6×N Jacobian approach because then the same computation engine and/or kinematic model that is used for other arms and instruments can also be used for the camera arm as well.

Accordingly, in some embodiments, Equations (2) and (3) discussed above may be modified. First, Equation (2) may be modified by using a number of phantom degrees of freedom corresponding to the missing degrees of freedom of the controlled mechanical body. This would extend the length of the (dq/dt) vector to equal to the sum of the numbers of existing degrees of freedom plus phantom degrees of freedom. For example, phantom degrees of freedom may be included in Equation (2), where those phantom DOF may be operable to control the wrist pitch and yaw for controlling the above-described endoscope. By using phantom degrees of freedom, the Jacobian based controller is faked into doing the pseudo-inverse calculation for a full six degree of freedom endoscope tip, i.e., a wristed endoscope. The output of this is a set of joint velocities for controlling a six degree of freedom endoscope, even though the actual endoscope being controlled only has four independently controllable degrees of freedom.

Second, in accordance with Equation (3), the joint positions are calculated by integrating joint velocities. However, Equation (3) may be modified such that the velocities of the phantom degrees of freedom, e.g., the nonexistent endoscope wrist joints, are not integrated and therefore remain at a fixed position. In some embodiments, the fixed or desired position may be set to any suitable value independent of a pose of the manipulator. For example, the fixed position may be set to 0 degrees, 15 degrees, 30 degrees, 45 degrees, a value in the range of 0 degrees to 45 degrees, a value less than 0 degrees or a value greater than 45 degrees.

By modifying Equations (2) and (3) for the control algorithm discussed above, in the embodiment concerning the endoscope the endoscope tip may consequently follow an instructed command well without unnecessary sluggishness. The unwristed endoscope has no wrist joints to actuate, and therefore the wrist may stay straight. Further, if there is a force reflection from the slave back to the masters, then the masters may be commanded to follow the straight tip of the endoscope, advantageously resulting in intuitive behavior.

In some embodiments, a pitch and yaw of the endoscope may be independently controlled, but the endoscope may not be able to independently roll. In response to an instruction to pan, a tip of the endoscope may be panned using only the pitch and yaw degrees of freedom. By using pitch and yaw, instead of translations and roll, the endoscope may be controlled to pan while substantially maintaining a location at an aperture of the patient. For example, the endoscope may be controlled to pan without increasing the size or placing pressure on an aperture of the patient through which the endoscope is disposed. This may be done, for example, by pivoting the endoscope about a pivot point at the aperture (i.e., access site).

It should be recognized that advantages are not limited to increasing the responsiveness of controlled tools and increasing the flexibility of the system by using the same controller to operate tools having different degrees of freedom. Rather, in some embodiments, advantages may be realized where tools may be actuated without requiring any additional degrees of freedom on an input device.

For example, in some embodiments, there may only be four inputs at the manipulator assembly, where three are typically used to control movement such as roll, pitch, and yaw, and the fourth is typically used to control a single actuation of an instrument (e.g. suction activation). However, it may be desired to control two actuations of an instrument (e.g., suction activation and irrigation activation) using the same number of inputs at the manipulator assembly. By using a kinematic model that calculates tool instructions using all three kinematic degrees of freedom, i.e., roll, pitch, and yaw, but then discarding one of the outputs, such as roll, motion of the tool may be controlled using only two inputs, i.e., pitch and yaw. The other two inputs may then be used to control two actuations of the instrument, such as suction activation and irrigation activation. Accordingly, although the instrument has only four degrees of freedom in total, including both movement and actuation degrees of freedom, as a result of using phantom degrees of freedom in the controller, the instrument appears to have five degrees of freedom. In some embodiments, phantom degrees of freedom may be used on axially symmetrical instruments, which may advantageously further increase the illusion to the operator of the system (e.g., a surgeon) that they are controlling a degree of freedom which actually may not exist in the instrument.

Returning now to FIG. 13, in operation 1310, the controller calculates the forward kinematics from the manipulator's joint positions. As a result of this calculation, the controller determines the commanded Cartesian space velocity ($dx_{des}/$ dt), the commanded Cartesian space position ($x_{des}$), the actual Cartesian space position (x), and the error between the latter two ($dx=x_{des}-x$). To calculate the forward kinematics, the controller may use the previously commanded joint position (e.g., the variable (q) calculated in an immediately preceding time step). In operation 1320, the controller calculates the desired move (dx/dt) using Equation (1). To calculate the desired move, the controller may use the output from step 1310 as well as the commanded end effector position ($x_{des}$). In operation 1330, the controller calculates the Jacobian (J), where calculating the Jacobian (J) uses the previously commanded joint position (q). In operation 1340, the controller calculates the pseudo-inverse of the Jacobian ($J^\#$).

In operation 1350, the controller calculates the joint-space velocity (dq/dt) using the pseudo-inverse of the Jacobian ($J^\#$) calculated in operation 1340 and using the desired move (dx/dt) calculated in operation 1320. The pseudo-inverse of the Jacobian in this operation includes phantom degrees of freedom as previously discussed. That is, the pseudo-inverse of the Jacobian includes mathematical representations of degrees of freedom of a mechanical body even though those degrees of freedom may not actually exist on the mechanical body being controlled by the controller. Then, in operation 1360, the controller calculates the joint-space commanded position (q) using Equation (3) and the joint-space velocity (dq/dt) calculated in operation 1350. However, as previously discussed, the velocities of the phantom degrees of freedom are not integrated in this operation and thus remain at (or may be set to) a fixed position.

Those skilled in the art would recognize that the operations discussed with reference to FIG. 13 may be executed frequently so as to provide real-time control of an instrument responsive to a user input. For example, the operations may be performed a plurality of times each second, in some embodiments about 1,000 times per second, 1,300 times per second, 1,500 times per second, in a range from 1,000 times per second to 1,500 times per second, less than 1,000 times per second or more than 1,500 times per second.

It should be appreciated that the specific operations illustrated in FIG. 13 provide a particular method of controlling manipulator arms, tools, and/or end effectors, according to certain embodiments of the present invention. Other sequences of operations may also be performed according to alternative embodiments. For example, alternative embodiments of the present invention may perform the operations outlined above in a different order. Moreover, the individual operations illustrated in FIG. 13 may include multiple sub-operations that may be performed in various sequences as appropriate to the individual operation. Furthermore, additional operations may be added or existing operations removed depending on the particular applications. One of ordinary skill in the art would recognize and appreciate many variations, modifications, and alternatives.

Figure 14:
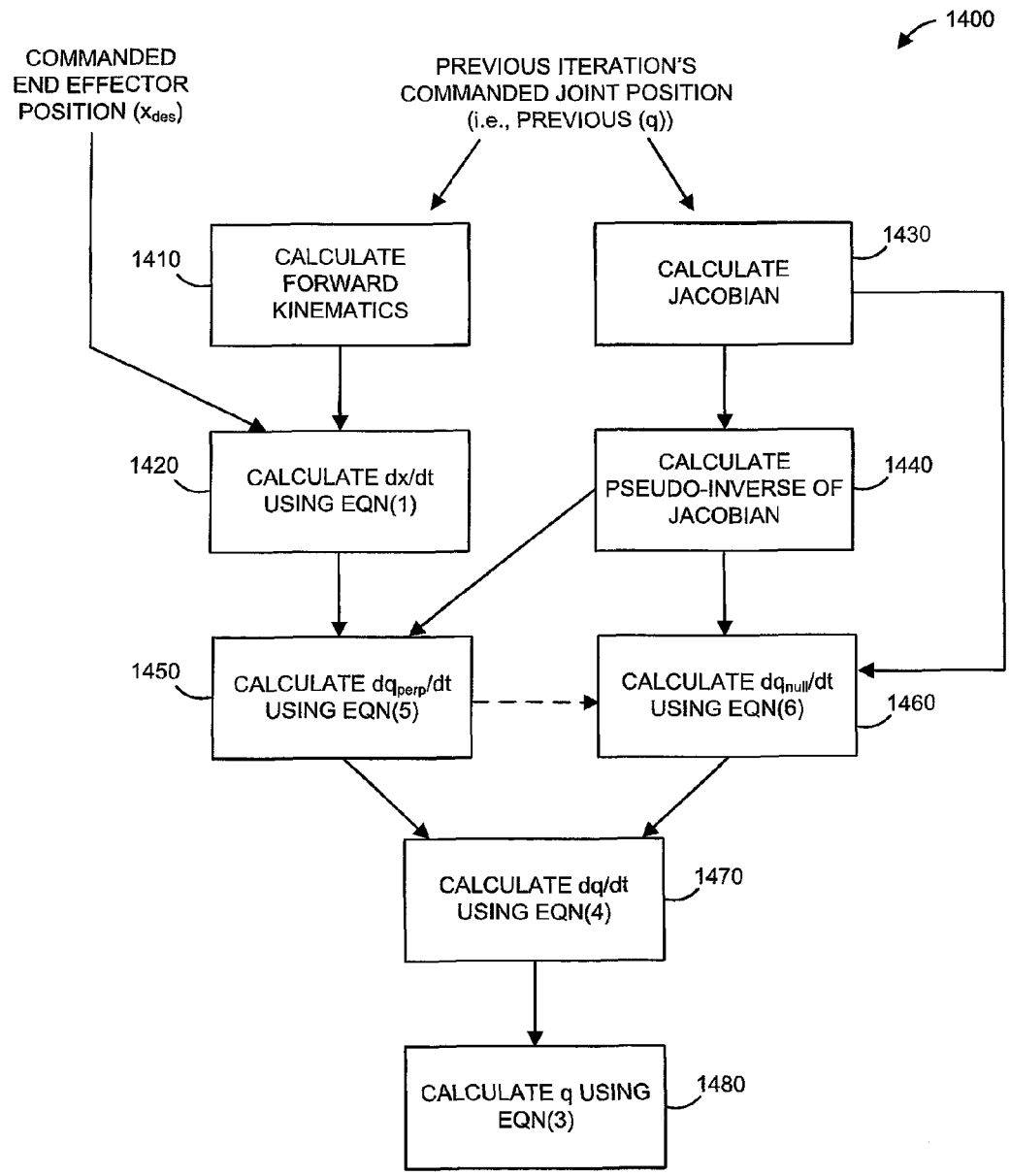
FIG. 14 is a flowchart showing a process for controlling manipulator arms, tools, and/or end effectors using an input device according to a second embodiment.

FIG. 14 is a flowchart showing a process 1400 for controlling manipulator arms, tools, and/or end effectors using an input device according to a second embodiment. The manipulator arms, tools, etc., input device and controller for executing the process 1400, may be similar to those described above with reference to FIG. 13, and thus further details are omitted.

In contrast to the process 1300 described with reference to FIG. 13, the process 1400 may be operable to calculate and control a null space of a Jacobian associated with a manipulator assembly. For example, the manipulator assembly may have one or more redundant degrees of freedom, but may still use one or more phantom joints where the manipulator assembly, even with its redundant degrees of freedom, lacks one or more of those degrees of freedom necessary to fully define the position of an end effector or tool.

Operations 1410 to 1440 are similar to operations 1310 to 1340 described with reference to FIG. 13, and thus further description is omitted. In operation 1450, the controller calculates the joint velocity component within the null-perpendicular-space ($dq_{perp}$/dt) using the pseudo-inverse of the Jacobian ($J^\#$) calculated in operation 1440 and the Cartesian space velocity (dx/dt) calculated in operation 1420. In operation 1460, the controller calculates the joint velocity component within the null-space ($dq_{null}$/dt) using the Jacobian calculated in operation 1430 and the pseudo-inverse of the Jacobian ($J^\#$) calculated in operation 1440 and shown in Equation (6), or in some embodiments, using the singular value decomposition of the Jacobian (SVD(J)) or, in some embodiments, using the null-space basis vectors ($V_n$) and blending coefficients ($\alpha$) as shown in Equation (6), or using any other equivalent technique. In at least one embodiment, the output of operation 1450 may be used to calculate the joint velocity component within the null-space ($dq_{null}$/dt) operation 1460. Similar to that discussed with reference to operation 1350 and Equation (2), the joint velocity component within the null-perpendicular-space ($dq_{perp}$/dt) and the joint velocity component within the null-space ($dq_{null}$/dt) may be calculated using phantom degrees of freedom in the Jacobian (e.g., in the pseudo-inverse of the Jacobian). Accordingly, each of these components of the joint-space velocity may be calculated using a Jacobian that mathematically represents degrees of freedom that may not actually exist in the controlled manipulator.

In operation 1470, the controller calculates the commanded joint-space velocity (dq/dt) by summing the joint velocity component within the null-perpendicular-space –($dq_{perp}$/dt) and the joint velocity component within the null-space ($dq_{null}$/dt) components calculated in operations 1450 and 1460 and as shown in Equation (4). Since each of the components of the commanded joint-space velocity (dq/dt) were calculated to include one or more phantom degrees of freedom, the resulting joint-space velocity (dq/dt) also includes one or more phantom degrees of freedom. Operation 1480 is then similar to operation 1360 described with reference to FIG. 13, and thus further description is omitted.

It should be appreciated that the specific operations illustrated in FIG. 14 provide a particular method of controlling manipulator arms, tools, and/or end effectors, according to certain embodiments of the present invention. Other sequences of operations may also be performed according to alternative embodiments. For example, alternative embodiments of the present invention may perform the operations outlined above in a different order. Moreover, the individual operations illustrated in FIG. 14 may include multiple sub-operations that may be performed in various sequences as appropriate to the individual operation. Furthermore, additional operations may be added or existing operations removed depending on the particular applications. One of ordinary skill in the art would recognize and appreciate many variations, modifications, and alternatives.

One skilled in the art would also recognize that while the processes of FIGS. 13 and 14 were described with reference to embodiments where input information is a desired position and comes from an input device (like the embodiments described with reference to FIGS. 10A to 10D), the processes may equally be applicable to embodiments where input information is an actual position and comes from a tool position measuring device (like the embodiments described with reference to FIGS. 11A and 11B). In such embodiments, instead of using a commanded end effector position ($x_{des}$) (e.g., as an input to operations 1320 and 1420), an actual end effector position would be used. And instead of generating a commanded joint position (q) (e.g., as an output of operation 1360 and 1480), an actual joint position would be generated.

The operations described in this application may be implemented as software code to be executed by one or more processors using any suitable computer language such as, for example, Java, C, C++ or Perl using, for example, conventional, sequential, or object-oriented techniques. The software code may be stored as a series of instructions, or commands on a computer-readable medium, such as a random access memory (RAM), a read-only memory (ROM), a magnetic medium such as a hard-drive or a floppy disk, flash memory, or an optical medium such as a CD-ROM. Any such computer-readable medium may also reside on or within a single computational apparatus, and may be present on or within different computational apparatuses within a system or network.

The present invention can be implemented in the form of control logic in software, firmware, or hardware or a combination of these. The control logic may be stored in an information storage medium as a plurality of instructions adapted to direct an information processing device to perform a set of steps disclosed in embodiments of the present invention. Based on the disclosure and teachings provided herein, a person of ordinary skill in the art will appreciate other ways and/or methods to implement the present invention.

The use of the terms "a" and "an" and "the" and similar referents in the context of describing embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope unless otherwise claimed. No language in the specification should be construed as indicating any non-claimed element as essential to the practice of at least one embodiment.

Preferred embodiments are described herein, including the best mode known to the inventors. Variations of those preferred embodiments may become apparent to those of ordinary skill in the art upon reading the foregoing description. The inventors expect skilled artisans to employ such variations as appropriate, and the inventors intend for embodiments to be constructed otherwise than as specifically described herein. Accordingly, suitable embodiments include all modifications and equivalents of the subject matter recited in the claims appended hereto as permitted by applicable law. Moreover, any combination of the above-described elements in all possible variations thereof is contemplated as being incorporated into some suitable embodiment unless otherwise indicated herein or otherwise clearly contradicted by context. The scope of the invention should, therefore, be determined not with reference to the above description, but instead should be determined with reference to the pending claims along with their full scope or equivalents.

What is claimed is:

1. A surgical system comprising:
   a surgeon's console including an input device for receiving an input from the surgeon;
   at least one manipulator structure operable to receive a first surgical instrument and a second surgical instrument, the first surgical instrument having a first number of degrees of freedom, the second surgical instrument having a second number of degrees of freedom, and the first number of degrees of freedom being different from the second number of degrees of freedom; and
   a controller for controlling at least one instrument coupled to the at least one manipulator structure,
   wherein the controller is operable to control the first surgical instrument and the second surgical instrument by using a first kinematic model of the first instrument and a second kinematic model of the second instrument, at least one of the first kinematic model or the second kinematic model including a phantom degree of freedom that models a range of joint configurations that are not included in the corresponding first instrument or second instrument.

2. The system of claim 1, wherein the first and second kinematic models each have a same number of degrees of freedom.

3. The system of claim 1, wherein the first kinematic model and the second kinematic model each define a 6×N Jacobian matrix.

4. The system of claim 1, wherein values for the phantom degree of freedom are discarded from an output of the corresponding first kinematic model or second kinematic model.

5. The system of claim 1, wherein the first surgical instrument and a corresponding manipulator structure together have a third number of degrees of freedom that excludes at least one degree of freedom necessary to fully define a position of the first surgical instrument.

6. The system of claim 5, wherein the second surgical instrument and a corresponding manipulator structure together have a fourth number of degrees of freedom that excludes at least two degrees of freedom necessary to fully define a position of the second surgical instrument.

7. The system of claim 1, wherein the first surgical instrument includes a camera, and the controller is operable to control a position of a tip of the camera.

8. The system of claim 7, wherein the controller is operable to cause the camera to pan or tilt by manipulating the pitch and yaw of the camera.

9. The system of claim 7, wherein the controller is operable to cause the camera to tilt by manipulating the camera to pan.

10. The system of claim 8, wherein the controller is operable to maintain a location of the camera at an aperture of a patient while causing the camera to pan.

11. The system of claim 1, wherein the first surgical instrument has at least one non-kinematic degree of freedom.

12. The system of claim 11, wherein the controller is operable to actuate the at least one non-kinematic degree of freedom instead of controlling a kinematic degree of freedom of the first surgical instrument.

* * * * *